United States Patent [19]  [11] 4,008,250
Bell et al. [45] Feb. 15, 1977

[54] CYCLOPENTA[c]PYRROLE DERIVATIVES

[75] Inventors: Malcolm R. Bell; Rudolf Oesterlin, both of East Greenbush, N.Y.

[73] Assignee: Sterling Drug Inc., New York, N.Y.

[22] Filed: Mar. 17, 1975

[21] Appl. No.: 558,807

Related U.S. Application Data

[63] Continuation-in-part of Ser. No. 346,005, March 29, 1973, Pat. No. 3,928,380.

[52] U.S. Cl. .................. 260/326.27; 260/247.2 R; 260/247.2 A; 260/247.2 B; 260/247.5 FP; 260/249.5; 260/250 AH; 260/250 BN; 260/251 R; 260/252; 260/279 R; 260/283 CN; 260/287 D; 260/288 CE; 260/293.61; 260/294.9; 260/304 D; 260/3 S; 260/306.7 T; 260/306.8 R; 260/306.8 D; 260/307 D; 260/308 D; 260/308 R; 260/310 R; 260/309.2; 260/310 C; 424/274; 424/273; 260/326.25; 424/270; 424/269; 260/315; 424/267; 424/263; 260/326.5 SA; 424/258; 424/257; 260/326.5 S; 424/253; 424/251; 260/326.5 B; 424/250; 424/249; 260/326.5 SF; 260/326.9; 260/326.62

[51] Int. Cl.$^2$ ..................................... C07D 309/52

[58] Field of Search .............. 260/326.62, 326.5 B, 260/326.27, 326.25

[56] References Cited

OTHER PUBLICATIONS

Jain et al.; Chem. Abs. vol. 53, 12275i (1959).

*Primary Examiner*—Donald G. Daus
*Assistant Examiner*—Mary C. Vaughn
*Attorney, Agent, or Firm*—William G. Webb; B. Woodrow Wyatt

[57] ABSTRACT

2,4,5,6-Tetrahydrocyclopenta[c]pyrrole-4-carboxamide and 4-thiocarboxamide derivatives useful as antisecretory and anti-ulcer agents are prepared by hydrolysis or thiohydrolysis of the corresponding 2,4,5,6-tetrahydrocyclopenta[c]pyrrole-4-carbonitriles or, in the case of the thiocarboxamides, by reaction of the 4-carboxamide with phosphorus pentasulfide.

38 Claims, No Drawings

4,008,250

CYCLOPENTA[c]PYRROLE DERIVATIVES

RELATED APPLICATIONS

This is a continuation-in-part of our prior, copending application Ser. No. 346,005, filed Mar. 29, 1973, now U.S. Pat. 3,928,380, patented Dec. 23, 1975.

BACKGROUND OF THE INVENTION a. Field of the Invention

This invention relates to 2,4,5,6-tetrahydrocyclopenta[c]pyrrole-4-carboxamides and thiocarboxamides useful as anti-secretory and anti-ulcer agents.

b. Description of the Prior Art

Although the 2,4,5,6-tetrahydrocyclopenta[c]pyrrole ring system is known (see for example Volz et al., Tetrahedron Letters 47, 4111-14 (1969) who disclose 1,3-dimethyl- and 1,2,3-trimethyl-4-oxo-2,4,5,6-tetrahydrocyclopenta[c]pyrrole and Berger et al., J. Org. Chem. 35, 3122 (1970) who disclose 1,3-dimethyl-4-oxo-2,4,5,6-tetrahydrocyclopenta[c]pyrrole), derivatives of such ring system having exocyclic functions, other than methyl groups at the 1-, 2- and 3-positions, have not been previously known. Furthermore the aforementioned prior art species are prepared by laborious multi-step synthetic methods and are not known to have any utility except as laboratory curiosities.

SUMMARY OF THE INVENTION

In one of its composition of matter aspects, the invention relates to certain 1,3-di-$R_6$-2-$R_7$-4-$R_3$-6-$R_4$-6-$R_5$-2,4,5,6-tetrahydrocyclopenta[c]pyrrole-4-carboxamides and thiocarboxamides where $R_3$, $R_4$, $R_5$, $R_6$ and $R_7$ are hydrogen, loweralkyl or other organic groups more specifically defined hereinafter, which are useful as anti-secretory and anti-ulcer agents.

In a second composition of matter aspect, the invention relates to certain 1,3-di-$R_6$-2-$R_7$-4-$R_3$-6-$R_4$-6-$R_5$-2,4,5,6-tetrahydrocyclopenta[c]pyrrole-4-carbonitriles which are useful as intermediates for the preparation of the corresponding 4-carboxamide final products.

In one of its process aspects, the invention relates to a process for preparing certain 1,3-di-$R_6$-2-$R_7$-4-$R_3$-6-$R_4$-6-$R_5$-2,4,5,6-tetrahydrocyclopenta[c]pyrrole-4-carboxamides comprising hydrolyzing the corresponding 4-carbonitriles.

In another of its process aspects, the invention relates to a process for preparing certain 1,3-di-$R_6$-2-$R_7$-4-$R_3$-6-$R_4$-6-$R_5$-2,4,5,6-tetrahydrocyclopenta[c]pyrrole-4-(N-$R_1$-N-$R_2$)-carboxamides comprising reacting the corresponding compounds where one or both of $R_1$ and $R_2$ are hydrogen with a strong base and reacting the resulting salt with an alkylating agent.

In another of its process aspects, the invention relates to a process for preparing certain 1,3-di-$R_6$-4,6,6-trimethyl-2,4,5,6-tetrahydrocyclopenta[c]pyrrole-4-carbonitriles comprising reacting an alkanedione, $R_6$-CO-$CH_2CH_2$-CO-$R_6$, with 2-amino-2-methylpropionitrile in an acid medium.

In another of its process aspects, the invention relates to a process for preparing certain 1,3-di-$R_6$-2-$R_7$-4,6,6-trimethyl-2,4,5,6-tetrahydrocyclopenta[c]pyrrole-4-carbonitriles comprising reacting a 1-$R_7$-2,5-di-$R_6$-substituted-pyrrole with 2-amino-2-methylpropionitrile.

In another of its process aspects, the invention relates to a process for preparing certain 1,3-di-$R_6$-2-$R_7$-4,6,6-trimethyl-2,4,5,6-tetrahydrocyclopenta[c]pyrrole-4-carbonitriles comprising reacting a 1-$R_7$-2,5-di-$R_6$-substituted-pyrrole with excess acetone in the presence of a mineral acid and reacting the resulting 3,3,3',3'-tetramethyl-4,4',6,6'-tetra-$R_6$-1,1'-spirobis(cyclopenta[4,5-c]pyrrole) with a source of ammonia and a source of cyanide ions in the presence of glacial acetic acid or with an equimolar amount of acetone.

In another of its process aspects, the invention relates to a process for preparing certain 1,3-diformyl-2-$R_7$-4-$R_3$-6-$R_4$-6-$R_5$-2,4,5,6-tetrahydrocyclopenta[c]pyrrole-4-carbonitriles comprising reacting the corresponding 1,3-dimethyl compounds with four moles of sulfuryl chloride and hydrolyzing the resulting 1,3-bis(dichloromethyl) compounds.

In another of its process aspects, the invention relates to a process for preparing certain 2-$R_7$-4-$R_3$-6-$R_4$-6-$R_5$-2,4,5,6-tetrahydrocyclopenta[c]pyrrole-4-carbonitriles unsubstituted at the 1- and 3-positions comprising decarbonylation of the corresponding 1,3-diformyl compound over a palladium-on-charcoal catalyst in an inert organic solvent.

In another of its process aspects, the invention relates to a process for preparing certain 1,3-di-$R_6$-4,6,6-trimethyl-2,4,5,6-tetrahydrocyclopenta[c]pyrrole-4-carbonitriles comprising reacting an alkanedione, $R_6$-CO-$CH_2CH_2$-CO-$R_6$, with acetone, a source of ammonia and a source of cyanide ions in an acid medium.

In another of its process aspects, the invention relates to a process for preparing certain 1,3-di-$R_6$-2-$R_7$-4,6,6-trimethyl-2,4,5,6-tetrahydrocyclopenta[c]pyrrole-4-carbonitriles comprising reacting a 1-$R_7$-2,5-di-$R_6$-substituted-pyrrole with acetone, a source of ammonia and a source of cyanide ions in an acid medium.

In another of its process aspects, the invention relates to a process for preparing certain 1,3-di-$R_6$-2-$R_7$-4-$R_3$-6-$R_4$-6-$R_5$-2,4,5,6-tetrahydrocyclopenta[c]pyrrole-4-carboxamides comprising oxidizing a corresponding 4-aldimide with oxygen.

In another of its process aspects, the invention relates to a process for preparing certain 1,3-di-$R_6$-2-$R_7$-4-$R_3$-6-$R_4$-6-$R_5$-2,4,5,6-tetrahydrocyclopenta[c]pyrrole-4-carboxamides comprising thermal or photochemical decomposition of a corresponding 1,3-di-$R_6$-2-$R_7$-4-$R_3$-6-$R_4$-6$R_5$-2,4,5,6-tetrahydrocyclopenta[c]pyrrole-4-(3-oxaziridine).

In another of its process aspects, the invention relates to a process for preparing certain 1,3-di-$R_6$-2-$R_7$-4-$R_3$-6-$R_4$-6-$R_5$-2,4,5,6-tetrahydrocyclopenta[c]pyrrole-4-carboxamides comprising oxidizing a corresponding 4-carbonitrile with hydrogen peroxide in a basic medium and decomposing the resulting perimidate by heating the reaction medium.

In another of its process aspects, the invention relates to a process for preparing certain 1,3-di-$R_6$-2-$R_7$-4,6,6-trimethyl-2,4,5,6-tetrahydrocyclopenta[c]pyrrole-4-carbonitriles comprising reacting with cyanide in glacial acetic acid a 1,3-di-$R_6$-2-$R_7$-4,4,6,6-tetramethyl-5,6-dihydro-1H-furo[3,4-c]pyrrole.

In another of its process aspects, the invention relates to a process for preparing certain 1-methyl-3-formyl-(and 1-formyl-3-methyl)-2-$R_7$-4-$R_3$-6-$R_4$-6-$R_5$-2,4,5,6-tetrahydrocyclopenta[c]pyrrole-4-carboxamides comprising oxidizing with oxygen a corresponding 1,3-dimethyl compound.

DETAILED DESCRIPTION INCLUSIVE OF THE PREFERRED EMBODIMENTS

More specifically, the invention relates to 2,4,5,6-tetrahydrocyclopenta[c]pyrrole-4-carboxamides and 4-thiocarboxamides, which are useful as anti-secretory and anti-ulcer agents and which have the Formula I:

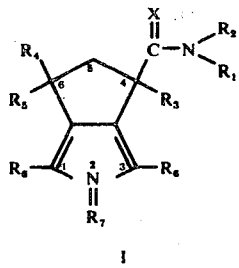

I where X is O or S; $R_1$ is hydrogen, lower-alkyl, di-lower-alkylamino-lower-alkyl, morpholino-lower-alkyl, 1-pyrrolidyl-lower-alkyl or 1-piperidyl-lower-alkyl; $R_2$ is hydrogen or lower-alkyl, or the group

can represent a 1-imidazolyl group; each of $R_3$, $R_4$ and $R_5$ is hydrogen or methyl; each $R_6$ group is the same of different hydrogen, formyl (CHO) and lower-alkane-1,3-diol ketals thereof, phenyl-lower-alkyl, carboxy, carbo-lower-alkoxy, lower-alkyl, or a group of the formula:

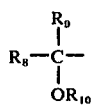

where $R_8$ is hydrogen, lower-alkyl, lower-alkenyl, lower-alkynyl, phenyl or phenyl-lower-alkyl; $R_9$ is hydrogen, cyano (CN), lower-alkyl, lower-alkenyl, lower-alkynyl, phenyl, phenyl-lower-alkyl, carboxy, carbo-lower-alkoxy, carbamyl ($CONH_2$), aminomethyl ($CH_2NH_2$), lower-alkanoyl, or trichloromethyl; $R_{10}$ is hydrogen, benzoyl, lower-alkanoyl, carboxy-lower-alkanoyl (and ammonium salts thereof) or lower-alkyl, $R_{10}$ being other than hydrogen only when either one or both of $R_8$ and $R_9$ are hydrogen and $R_8$ being cyano only when $R_{10}$ is hydrogen; and $R_7$ is hydrogen, lower-alkyl, halo-lower-alkyl, lower-alkenyl, lower-alkynyl, di-lower-alkyl-amino-lower-alkyl, morpholino-lower-alkyl, 1-pyrrolidyl-lower-alkyl, 1-piperidyl-lower-alkyl, carbo-lower-alkoxy-lower-alkyl, carboxy-lower-alkyl, carboxamido-lower-alkyl, thiocarboxamido-lower-alkyl, lower-alkoxy-lower-alkyl, hydroxy-lower-alkyl, lower-alkyl-thio-lower-alkyl, cycloalkyl, cycloalkyl-lower-alkyl, 2- or 3-pyridyl, phenyl, phenyl-lower-alkyl, thienyl, 9-acridinyl, 4-(2,1,3-benzothiadiazolyl), 2-benzothiazolyl, 3-carbazolyl, 2-benzoxazolyl, 2- or 6-purinyl, 2-pyrazinyl, 4-pyrimidinyl, 2-thiazolyl, 3-pyrazolyl, 2- or 6-pyrimidinyl, 2-benzimidazolyl, 2-benzothiazolyl, 5-, 6- or 7-indazolyl, 5-isoquinolinyl, 3-pyridazinyl, 2-thiadiazolyl, 5-tetrazolyl, 2-thiazolinyl, 3-(1,2,4-triazinyl), 3-(1,2,4-triazolyl), or divalent-lower-alkylene having its valences on different carbon atoms and joining two of the 2,4,5,6-tetrahydrocyclopenta[c]pyrrole moieties together, and wherein the phenyl or phenyl-lower-alkyl groups can be further substituted in the phenyl nucleus by a single methylenedioxy or from one to three members of the group consisting of lower-alkyl, lower-alkoxy, halogen (including fluorine, bromine and chlorine), hydroxy, trifluoromethyl lower-alkanoylamino, amino, di-lower-alkylamino, carboxyl, carboxamido, carbo-lower-alkoxy, lower-alkylmercapto, lower-alkylsulfinyl, lower-alkylsulfonyl, nitro and sulfamoyl.

Preferred compounds within the ambit of Formula I are those where X is O; each of $R_1$ and $R_2$ is hydrogen or lower-alkyl; each of $R_3$, $R_4$ and $R_5$ is hydrogen or methyl; both $R_6$ groups are lower-alkyl; an $R_7$ is lower-alkyl or phenyl and also the compounds of formula I where X is O; $R_1$ and $R_2$ are each hydrogen; $R_3$, $R_4$ and $R_5$ are each methyl; one $R_6$ is hydrogen, lower-alkyl or hydroxymethyl and the other is hydrogen, lower-alkyl or the group:

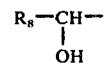

where $R_8$ is hydrogen, lower-alkyl, lower-alkenyl, or lower-alkynyl; and $R_7$ is phenyl (or substituted-phenyl), both of which preferred groups are represented by the formula:

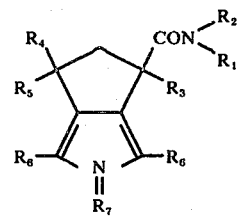

As used herein the terms lower-alkyl and lower-alkoxy mean saturated, monovalent, aliphatic radicals, including straight or branched-chain radicals, of from one to four carbon atoms as illustrated by, but not limited to, methyl, ethyl, propyl, isopropyl, butyl, sec.-butyl, isobutyl, methoxy, ethoxy, propoxy, isopropoxy, butoxy, isobutoxy, and the like.

As used herein the term cycloalkyl means saturated carbocyclic groups containing from three to six ring carbon atoms and having a total of 5 to 10 carbon atoms, as illustrated by, but not limited to, cyclopropyl, cyclobutyl, 2-methylcyclobutyl and cyclohexyl.

As used herein the terms lower-alkenyl and lower-alkynyl mean monovalent, aliphatic radicals of from 3 to 6 carbon atoms which contain at least one double or triple bond, and are either straight or branched-chain as illustrated by, but not limited to, 1-(2-propenyl), 1-(1-propenyl), 1-(3-methyl-2-propenyl), 1-(1,3-dimethyl-2-propenyl), 1-(2-hexenyl), 1-(2-propynyl) and 1-(2-butynyl).

As used herein, the term lower-alkylene means divalent, aliphatic radicals, including straight or branched-chain radicals, or from 2 to 8 carbon atoms, and having its valences on different carbon atoms as illustrated by, but not limited to, 1,2-ethylene, 1,4-butylene, 1,6-hexylene, 3-methyl-1,5-pentylene and 1,8-octylene.

The compounds of Formula I where X is O; $R_1$ and $R_2$ are each hydrogen; and $R_3$, $R_4$, $R_5$, $R_6$ and $R_7$ have the meanings given above are prepared by hydrolysis, under acid, basic or neutral conditions, of the corresponding 2,4,5,6-tetrahydrocyclopenta[c]pyrrole-4-carbonitriles having the Formula II:

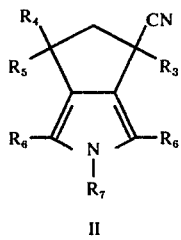

II where $R_3$, $R_4$, $R_5$ and $R_6$ have the meanings given above, and $R_7$, in addition to the various meanings given above, represents cyano-lower-alkyl. Hydrolysis under basic conditions is advantageously effected by warming a solution of the nitrile of Formula II in an inert organic solvent, for example methanol, ethanol or isopropanol, containing a molar excess of an alkali metal hydroxide. Hydrolysis in a neutral medium is advantageously carried out using the procedure of Bennett et al., J. Am. Chem. Soc. 95, 3030-1 (1973) in which a planar, nonionic tertiary phosphine metal-hydroxy complex is used as a catalyst. Hydrolysis in an acid medium is carried out by heating a solution of the nitrile in a mineral acid, for example, phosphoric acid, polyphosphoric acid or aqueous sulfuric acid at a temperature from 0° C. to around 70° C. During the reaction, the nitrile group in the compounds of Formula II where $R_7$ is cyano-lower-alkyl is hydrolyzed simultaneously with the nitrile group attached to the 4-position of the 2,4,5,6-tetrahydrocyclopenta[c]pyrrole to thus produce compounds of Formula I where $R_7$ is carboxamido-lower-alkyl, and the above-described procedure constitutes a preferred method of preparing the latter compounds.

The compounds of Formula I where X is S; $R_1$ and $R_2$ are each hydrogen; and $R_3$, $R_4$, $R_5$, $R_6$ and $R_7$ have the meanings given above are preferably prepared by thiohydrolysis of the nitriles of Formula II using the procedure of Karrer et al., Helv. Chim. Acta 28, 820 (1945) which involves reacting the nitrile with a saturated solution of ammonia and hydrogen sulfide in an organic solvent, preferably a lower-alkanol, at room temperature. Alternatively, the reaction can be carried out under pressure in an autoclave at a temperature from 150°-160° C. using the procedure described by Ralston et al., J. Org. Chem. 4, 68 (1939). As in the case of the hydrolysis of the compounds of Formula II to those of Formula I where X is O, thiohydrolysis of the compounds of Formula II where $R_7$ is cyano-lower-alkyl affords the compounds of Formula I where $R_7$ is thiocarboxamido-lower-alkyl, and the above-described procedure constitutes a preferred method of preparing the latter compounds.

Alternatively, and preferably, the compounds of Formula I where X is S are prepared by reaction of the corresponding compounds where X is O with phosphorus pentasulfide. The reaction is carried out by heating the reactants directly either with or without a solvent. Preferred solvents, when used, are benzene, toluene, xylene, dioxane and the like.

The compounds of Formula I where $R_7$ is other than hydrogen can also be prepared by reaction of the corresponding compounds where $R_7$ is hydrogen with a strong base, for example alkali metal hydrides or alkali metal amides, in an inert organic solvent, for example dimethylsulfoxide, dioxane, dimethylformamide, tetrahydrofuran, dibutyl ether, and the like, and reaction of the resulting salt with an appropriate alkylating agent, $R_7X$, where X is the anion of a strong mineral acid, for example a hydrogen halide or sulfuric acid, and $R_7$ has the meanings given above. The reaction is preferably carried out at low temperatures, i.e. from 0° C. to about 40° C. During the reaction, alkylation can take place at either the amide nitrogen atom, when compounds where $R_1$ and $R_2$ are both hydrogen are used as starting materials, or at the pyrrole nitrogen atom, and it is possible to isolate both isomeric products from the reaction mixture.

The compounds of Formula I where $R_7$ is lower-alkenyl are preferably prepared by Hofmann elimination of a tertiary amine from a compound of Formula I where $R_7$ is di-lower-alkylamino-lower-alkyl, morpholino-lower-alkyl, 1-pyrrolidyl-lower-alkyl or 1-piperidyl-lower-alkyl. The method comprises converting the tertiary amine to a quaternary ammonium salt by reaction of the amine with an ester of a strong inorganic acid, e.g. a lower-alkyl halide or a di-lower-alkyl sulfate, and reacting the quaternary salt with silver oxide, preferably in an aqueous medium to effect conversion of the quaternary slt to the corresponding ammonium hydroxide, which spontaneously decomposes in an aqueous medium at ambient temperature to the N-lower-alkenyl-substituted compound of Formula I and a tertiary amine. It is preferred to use a dimethylamino-lower-alkyl-substituted compound of Formula I as starting material and a methyl halide or dimethyl sulfate as quaternizing agent.

The compounds of Formula I where $R_1$ and/or $R_2$ are other than hydrogen and $R_7$ is other than hydrogen are prepared by reacting the corresponding carboxamides where either one or both of $R_1$ and $R_2$ are hydrogen with a strong base, for example an alkali metal hydride or an alkali metal amide, followed by reaction of the resulting salt with an alkylating agent, for example a lower-alkyl halide or a di-lower-alkyl sulfate. As indicated above, when compounds where both $R_1$ and $R_2$ are hydrogen are used as starting materials, alkylation can take place on both the ring and amide nitrogen atoms, necessitating separation of the isomeric products. Preparation of the compounds where both $R_1$ and $R_2$ are lower-alkyl is best effected by stepwise alkylation of the carboxamide, that is alkylation of the compounds where both $R_1$ and $R_2$ are hydrogen using one mole of a strong base and one mole of an alkylating agent followed by a second alkylation of the resulting N-lower-alkylcarboxamide where one of $R_1$ and $R_2$ is lower-alkyl. The reaction with a second mole of strong base takes place under much more vigorous conditions involving use of higher reaction temperatures, i.e. from about 50° C. to about 150° C., and longer reaction times than the above-described method for alkylation at the pyrrole nitrogen atom or monoalkylation at the amide nitrogen atom, which take place at lower temperatures and shorter reaction times. The reaction is carried out in an inert organic solvent, for example dimethylsulfoxide, dioxane, dimethylformamide, tetrahydrofuran, dibutyl ether, and the like.

The compounds of Formula I where one or both $R_6$ groups are hydroxymethyl ($R_8$, $R_9$ and $R_{10}$ are hydrogen), are prepared by reduction, with an alkali metal borohydride, of the corresponding compounds of Formula I where one or both $R_6$ groups are formyl. The reaction is carried out in an inert organic solvent, for example lower-alkanols, dioxane, diethyl ether, and the like. The reaction generally takes place at ambient temperature, although elevated temperatures up to the boiling point of the solvent can be used to expedite the reaction. The method for the preparation of compounds where both $R_6$ groups are hydroxymethyl is represented by the equation:

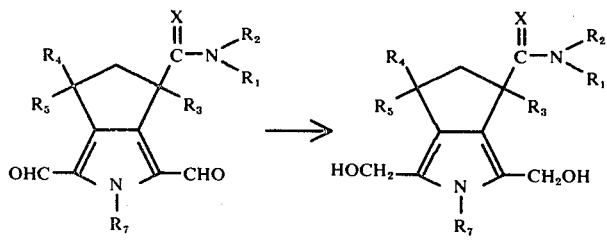

Where $R_1$, $R_2$, $R_3$, $R_4$, $R_5$, $R_7$, and X have the meanings given above.

The compounds of Formula I where one or both $R_6$ moieties is the group

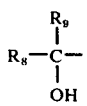

where $R_8$ is hydrogen and $R_9$ is lower-alkyl, lower-alkynyl, lower-alkenyl, phenyl, phenyl-lower-alkyl or trichloromethyl are prepared by reaction of the corresponding compound where one or both $R_6$ groups is formyl with an organo metallic compound such as an organo lithium, e.g. a lower-alkyl, lower-alkenyl, lower-alkynyl or phenyl lithium, or an organo magnesium halide, e.g. phenyl (or substituted-phenyl) magnesium halide or a phenyl-lower-alkyl magnesium halide, and hydrolysis of the resulting organometallic compound. The reaction is carried out in an inert organic solvent such as tetrahydrofuran or diethyl ether.

The compounds of Formula I where $R_8$ is lower-alkyl, lower-alkynyl, lower-alkenyl, phenyl or phenyl-lower-alkyl and $R_9$ is the same or different lower-alkyl, lower-alkynyl, lower-alkenyl, phenyl or phenyl-lower-alkyl are prepared by reacting the corresponding compounds where $R_6$ is carbo-lower-alkoxy with either four molar equivalents of an organo metallic compound as indicated above, which affords compounds where $R_8$ and $R_9$ are identical, or if desired only two moles of the organo metallic compound can be used which affords compounds where $R_6$ is a ketone group, i.e. $R_8$-CO (or $R_9$-CO). The latter is then reacted with two moles of a different organo metallic compound to give the carbinols where $R_8$ and $R_9$ are different. In each of the above-described reactions requiring use of an organo metallic compound, one mole of the organo metallic reagent in addition to that required for reaction at the 1- or 3-positions is required when the compounds of Formula I where one or both of $R_1$ and $R_2$ is hydrogen is used as the starting material, because one mole of the organo metallic reagent reacts with one of the protons on the amide nitrogen.

The compounds of Formula I where $R_9$ is cyano, carbamyl or aminomethyl are prepared via the cyanohydrin (i.e. $R_9$ is cyano) of the corresponding compounds where $R_6$ is formyl. The cyanohydrins are prepared by reaction of the formyl compounds with diethyl aluminum cyanide in an inert organic solvent, for example benzene, toluene, xylene, tetrahydrofuran, dioxane or mixtures of these solvents. A preferred solvent is a mixture of benzene and tetrahydrofuran. The cyanohydrins in turn, on either hydrolysis with dilute sulfuric acid using the same conditions as described for hydrolysis of the compounds of Formula II to Formula I, or catalytic reduction with hydrogen over platinum oxide afford, respectively, the compounds where $R_9$ is carbamyl an aminomethyl.

The compounds of Formula I where $R_9$ is carboxy or carbo-lower-alkoxy are prepared by hydrolysis of the corresponding compounds where $R_9$ is trichloromethyl, using the procedure described below for preparing the compounds where $R_6$ is formyl or carboxy, to afford the compounds where $R_9$ is carboxy. The esters are prepared from the acids by standard esterification procedures.

The compounds of Formula I where $R_9$ is lower-alkanoyl are prepared by hydroxylation of the corresponding compounds where $R_9$ is lower-alkynyl using dilute sulfuric acid.

The compounds of Formula I where $R_{10}$ is lower-alkyl are prepared by reacting the free carbinols ($R_{10}$ is hydrogen) with a lower-alkanol in the presence of a mineral acid. The compounds where $R_{10}$ is an ester group, i.e. benzoyl, lower-alkanoyl or carboxy-lower-alkanoyl are prepared by reacting the carbinol either with an acid halide or an acid anhydride in the presence of an acid acceptor, for example pyridine or a tri-lower-alkylamine.

The intermediate 2,4,5,6-tetrahydrocyclopenta[c]pyrrole-4-carbonitriles of Formula II are prepared by a variety of different methods depending upon the identities of the various $R_3$, $R_4$, $R_5$, $R_6$ and $R_7$ groups. For example, the nitriles where $R_3$, $R_4$ and $R_5$ are each methyl, one or both $R_6$ groups are lower-alkyl or phenyl-lower-alkyl, and $R_7$ is hydrogen, which are represented by Formula IIa, are prepared by reaction of an alkanedione (or diphenylalkanedione), in which the two keto groups are separated by two carbon atoms as represented by Formula III, with 2-amino-2-methylpropionitrile having the Formula IV. The method is represented by the reaction:

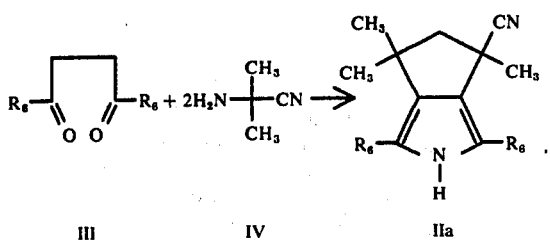

III    IV    IIa where $R_6$ has the meanings given above, and takes place in an acid medium, preferably a lower-alkanoic acid, particularly glacial acetic acid. Surprisingly, the reaction does not produce a pyrrole derivative having an α,α-dimethylacetonitrile group attached to the nitrogen atom of the pyrrole ring, as might be expected, but instead affords the 2,4,5,6-tetrahydrocyclopenta[c]pyrrole derivatives of Formula IIa above-indicated. The reaction is preferably carried out in the presence of a stoichiometric amount of a stronger acid, for example, fluoroacetic acid (preferred, trichloroacetic acid or phosphoric acid.

Alternatively, the same transformation can be effected by use of excess acetone and a source of ammonia, e.g. an ammonium salt such as ammonium acetate, and a source of cyanide ion, e.g. an alkali metal cyanide, in place of the 2-amino-2-methylpropionitrile. The reaction is carried out under the same conditions described above for the reaction based on 2-amino-2-methylpropionitrile.

Alternatively, the compounds of Formula II where $R_3$, $R_4$ and $R_5$ are each methyl, one or both $R_6$ groups are lower-alkyl or phenyl-lower-alkyl, and $R_7$ has the various meanings given above, which are represented by Formula IIb below, can be prepared by reaction of 2-amino-2-methylpropionitrile having the Formula IV above or acetonecyanohydrin having the formula:

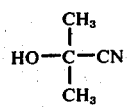

with a 1-$R_7$-2,5-di-$R_6$-substituted-pyrrole having the Formula V using the same reaction conditions as described above for the preparation of the compounds of Formula IIa using the alkanedione route. In addition, the presence of a strong organic acid such as chloro- acetic acid or trifluoroacetic acid is desirable. The method is represented by the reaction:

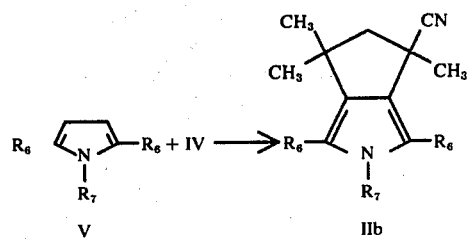

V    IIb where $R_6$ and $R_7$ have the meanings given above.

Alternatively, the same transformation can be effected by use of excess acetone, along with a source of ammonia, e.g. an ammonium salt such as ammonium acetate, and a source of cyanide ion, e.g. an alkali metal cyanide, in place of the 2-amino-2-methylpropionitrile. The reaction is carried out under the same conditions described above for the reaction based on 2-amino-2-methylpropionitrile.

The 1-$R_7$-2,6-di-$R_6$-substituted-pyrroles of Formula V where one or both $R_6$ groups are lower-alkyl or phenyl-lower-alkyl are in turn prepared by reacting an alkanedione or diphenylalkanedione having the Formula III above with an appropriate amine, $R_7NH_2$, under dehydrating conditions. The reaction is preferably carried out by refluxing the reactants in a water-immiscible organic solvent, for example benzene, toluene or xylene, using a water separator, i.e. a Dean-Stark trap, to separate the water and remove it from the reaction medium as it is formed during the reaction.

Alternatively, the compounds of Formula II where $R_3$, $R_4$ and $R_5$ are methyl, one or both $R_6$ groups are lower-alkyl or phenyl-lower-alkyl, and $R_7$ has the various meanings given above, which are represented by Formula IIb, are prepared by condensation of a 1-$R_7$-2,5-di-$R_6$-substituted-pyrrole of Formula V with excess acetone in the presence of a source of cyanide ion, e.g. an alkali metal cyanide, and a molar excess of a mineral acid, for example hydrochloric acid or sulfuric acid. The resulting 3,3,3',3'-tetramethyl-4,4',6,6'-tetra-$R_6$-1,1'-spirobis(cyclopenta[4,5-c]pyrrole) of Formula VI is then reacted with a source of ammonia, e.g. ammonium acetate, and a source of cyanide ions, e.g. an alkali metal cyanide, in the presence of glacial acetic acid. The initial condensation of the 1-$R_7$-2,5-di-$R_6$-substituted-pyrrole of Formula V with acetone preferably takes place by short refluxing of the reactants, The method is represented by the following reactions:

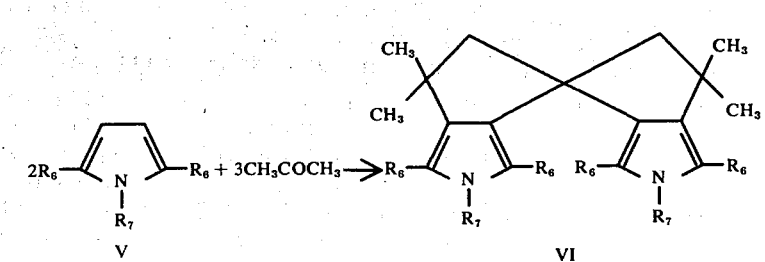

V    VI

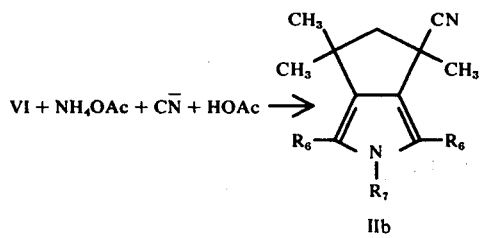

where $R_6$ and $R_7$ have the meanings given above. Alternatively, the compounds of Formula IIb are prepared by reaction of one mole of a compound of Formula VI with one mole of acetone.

Alternatively, the 3,3,3′,3′-tetramethyl-4,4′,6,6′-tetra-$R_6$-1,1′-spirobis(cyclopenta[4,5-c]pyrroles) of Formula VI can be prepared by reaction of a 1-$R_7$-2,5-di-$R_6$-substituted-pyrrole of Formula V with a molar excess of 2-amino-2-methyl propionitrile of Formula IV, preferably in the presence of a strong organic acid using the same conditions as described above for the preparation of the compounds of Formula IIb from a 1-$R_7$-2,5-di-$R_6$-substituted-pyrrole of Formula V and 2-amino-2-methylpropionitrile of Formula IV. In fact, the spiro compounds can often be isolated as a by-product in the latter process.

The compounds of Formula II where both $R_6$ groups are formyl are prepared by reaction of the compounds of Formula IIc, where both $R_6$ groups are methyl and $R_3$, $R_4$, $R_5$ and $R_7$ have the meanings given above, with four moles of sulfuryl chloride, which affords the corresponding compounds where each $R_6$ group is dichloromethyl ($Cl_2CH$), represented by Formula IId, followed by hydrolysis of the latter with water and a water miscible organic solvent, which only serves to promote solution of the starting material, for example dioxane, acetone, ethylene glycol, or a lower-alkanol, to give the corresponding compounds where both $R_6$ groups are formyl, which are represented by Formula IIe. The method is represented by the following reactions:

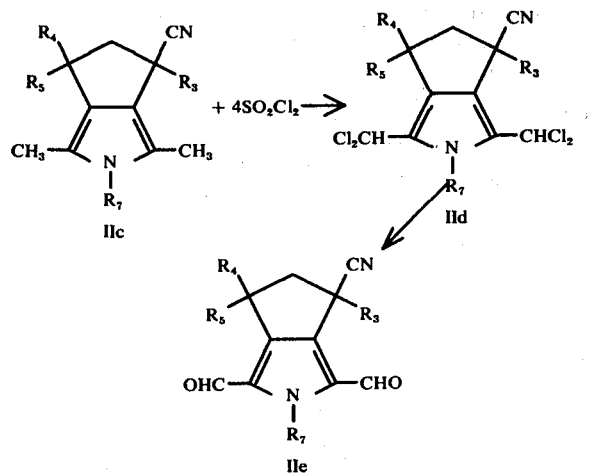

where $R_3$, $R_4$, $R_5$ and $R_7$ have the meanings given above.

The 1,3-diformyl compounds of Formula IIe are particularly valuable intermediates for the preparation of the final products of Formula I in which the two $R_6$ moieties are different, because one of the two formyl groups can be individually protected while other transformation are carried out on the other formyl group after which the protecting group can be removed to regenerate the formyl group which can then either be preserved in the final products or if desired utilized as a handle for conversion to other groups such as various carbinols as described above. A particularly effective means of protecting one of two formyl groups is to cnvert the latter to a ketal by reaction of the formyl derivative with one molar equivalent of an alkanediol (or with two molar equivalents of a lower-alkanol) in an anhydrous medium and in the presence of a strong acid. Preferred alkanediols are 1,3-propanediols which may be straight or branched, for example, 2,2-dimethylpropanediol or 1,1,3-trimethyl-1,3-propanediol (i.e. 2-methylpentane-2,4-diol). The resulting mixture of products containing a ketal group at each of the 1- and 3-positions can, if desired, be separated into the individual components, and each component treated separately in subsequent synthetic steps. The unprotected formyl group can then, for example, be oxidized to the carboxylic acid using an alkaline medium in which the ketal group is stable, for example alkaline permanganate. The carboxyl group thus produced can either be retained as such or converted to an ester moiety or, if desired, it can be removed by heating the product at a temperature of around 200°–250° C. in a high boiling organic solvent, for example dimethylaniline, ethylene glycol or propylene glycol.

The compounds of Formulas I and II where one or both $R_6$ groups are carboxy are prepared by oxidizing the corresponding compounds where one or both $R_6$ groups are formyl with one mole of an oxidizing agent per formyl group, for example alkaline permanganate as described above. The corresponding compounds of Formulas I and II where one $R_6$ group is formyl and the other a carboxy group can also be prepared by reaction of the corresponding compound of Formula I or II where both $R_6$ groups are methyl with five molar equivalents of sulfuryl chloride, which affords the compounds where one $R_6$ group is dichloromethyl and the other trichloromethyl, and hydrolysis of the latter with water in a water-miscible organic solvent as described above. The compounds where one or both $R_6$ groups are carbo-lower-alkoxy are prepared from compounds wherein one or both $R_6$ groups are carboxy by standard esterification procedures comprising reacting the carboxylic acid with a lower-alkanol.

The compounds of Formula II where one or both $R_6$ groups are hydrogen, which are represented by Formula IIf, are prepared by decarbonylation of the corresponding compounds where one or both $R_6$ groups are formyl, which are represented by Formual IIe above, over a palladium-on-charcoal catalyst. The reaction is carried out in an inert organic solvent, preferred solvents being glycols having a boiling point around 200°

C. or higher, for example ethylene glycol, propylene glycol, glycerol, and the like. The reaction is preferably carried out at an elevated temperature, i.e. at the boiling point of the solvent used, which serves to shorten the reaction time but is otherwise not critical. The reaction is represented by the equation:

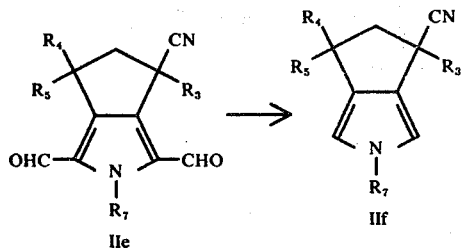

where $R_3$, $R_4$, $R_5$ and $R_7$ have the meanings given above. For the sake of brevity, the reaction is shown as involving the decarbonylation of formyl groups at both the 1- and 3-positions, but it is to be understood that the method can be used to effect decarbonylation of compounds having formyl groups at either one or both of the 1- and 3-positions of the compounds of Formula II. Moreover, although the method is shown as being applied only to the compounds of Formula II, decarbonylation at either or both of the 1- and 3-positions can also be carried out on the final products of Formula I.

The compounds of Formula II where $R_3$ is lower-alkyl; $R_4$ and $R_5$ are hydrogen; one or both $R_6$ groups are lower-alkyl or phenyl-lower-alkyl; and $R_7$ has the various meanings given above, which are represented by Formula IIg below, are prepared by a sequence of reactions involving, first, conversion of a 1-$R_7$-2,5-di-$R_6$-substituted-pyrrole of Formula V to the corresponding 3-formyl derivative having the Formula VIII by the Vilsmeier-Haack reaction, which comprises reacting the pyrrole with dimethylformamide in the presence of phosphorus oxychloride at a temperature in the range from 50°–100° C. and decomposition of the mixture with aqueous sodium acetate; conversion of the formyl compound to the corresponding 3-acrylonitrile derivative of Formula IX by reaction of the formyl derivative with sodium hydride in dimethylformamide, followed by reaction of the resulting sodium salt with diethoxy-phosphonoacetonitrile

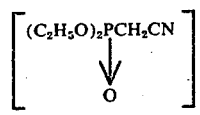

in ethylene glycol dimethyl ether; catalytic reduction of the resulting acrylonitrile derivative to the corresponding propionitrile derivative of Formula X; hydrolysis of the latter with methanolic potassium hydroxide to the corresponding propionic acid; cyclization of the latter by heating with polyphosphoric acid; and reaction of the resulting 4-oxo-2,4,5,6-tetrahydro-1,3-di-$R_6$-2-$R_7$-cyclopenta[c]pyrrole of Formula XI with a lower-alkyl magnesium halide followed by heating the resulting carbinol with a molar excess of a 1:1 mixture of potassium cyanide and potassium acetate in glacial acetic acid. The method is represented by the following reactions:

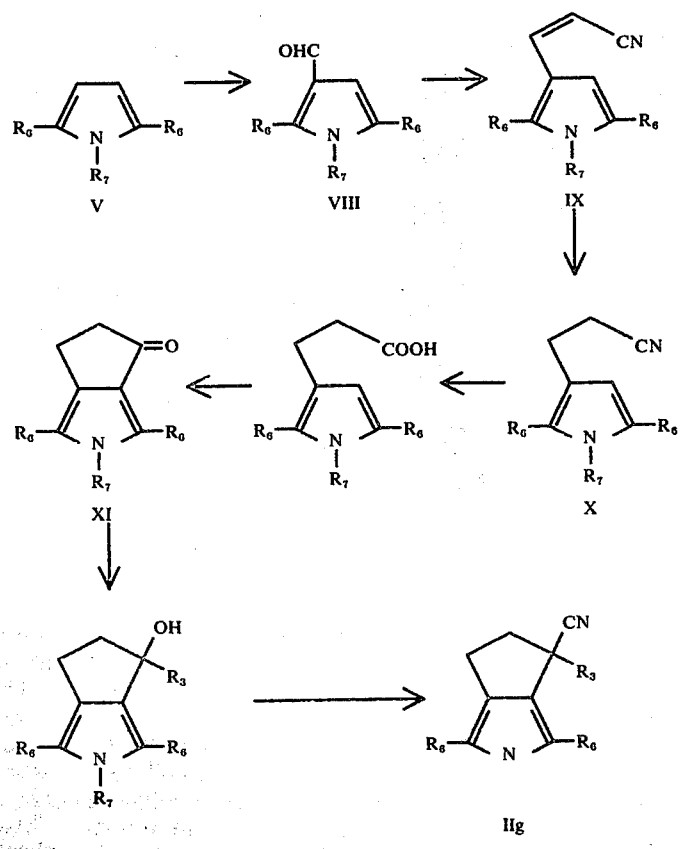

where $R_3$, $R_6$ and $R_7$ have the meanings given above.

This same general approach can be utilized to prepare the compounds of Formula II where $R_3$ and $R_4$ are either hydrogen or the same or different lower-alkyl. Thus, reaction of a 1-$R_7$-2,5-di-$R_6$-pyrrole with either dimethylformamide ($R_4$ is hydrogen) or a dimethyl-alkanamide ($R_4$ is lower-alkyl) in the presence of phosphorus oxychloride; reaction of the resulting 1-$R_7$-2,5-di-$R_6$-4-$R_4$CO-pyrrole with ethyl diethoxyphosphonoacetate in ethylene glycol dimethyl ether; catalytic reduction of the resulting ethyl acrylate derivative to the corresponding ethyl propionate; hydrolysis of the latter to the corresponding propionic acid; cyclization of the latter by heating with polyphosphoric acid; and either reaction of the resulting 4-oxo-2,4,5,6-tetrahydro-1,3-di-$R_6$-2-$R_7$-cyclopenta[c]pyrrole with a lower-alkyl magnesium halide ($R_3$ is lower-alkyl) or by reduction of the former with sodium borohydride, followed in either case by heating the resulting carbinol with a molar excess of a 1:1 mixture of potassium cyanide and potassium acetate in glacial acetic acid. The method is represented by the following reaction sequence:

the reflux temperature of the reaction mixture. The method is represented by the following reaction sequence:

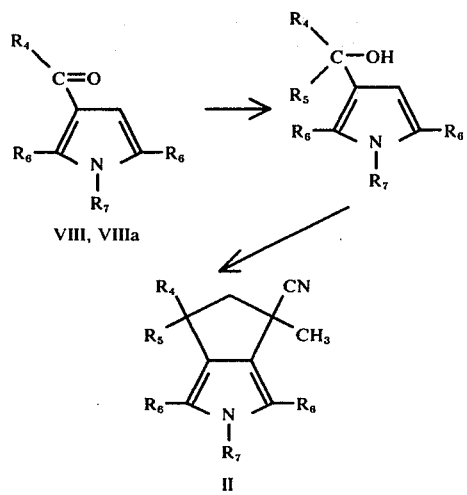

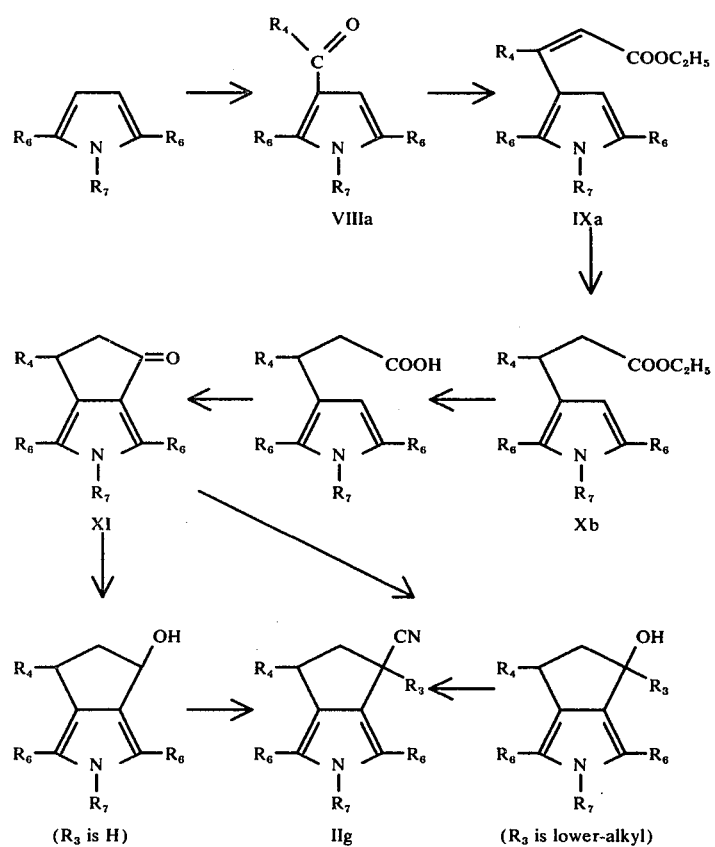

where $R_3$, $R_4$, $R_6$ and $R_7$ have the meanings given above.

The compounds of Formula II where $R_3$ is methyl and $R_4$ and $R_5$ are either hydrogen or lower-alkyl can also be prepared by reaction of a 1-$R_7$-2,5-di-$R_6$-4-$R_4$CO-pyrrole of formulas VIII ($R_4$ is hydrogen) or VIIIa ($R_4$ is lower-alkyl) with a lower-alkyl magnesium halide ($R_5$ is lower-alkyl) or reduction of the ketone to the carbinol with sodium borohydride ($R_4$ and $R_5$ are both hydrogen) and reaction of the resulting carbinol with one molar equivalent of acetone and two molar equivalents each of potassium cyanide and potassium acetate in glacial acetic acid. The latter reaction is carried out at the reflux temperature of the reaction mixture. The where $R_4$, $R_5$, $R_6$ and $R_7$ have the meanings given above.

The compounds of Formula II where $R_3$, $R_4$ and $R_5$ have all the various meanings given above, one or both $R_6$ groups are hydrogen, lower-alkyl or phenyl-lower-alkyl, and $R_7$ is lower-alkyl, di-lower-alkylamino-lower-alkyl, morpholino-lower-alkyl, 1-pyrrolidyl-1-lower-alkyl, 1-piperidyl-lower-alkyl, cycloalkyl-lower-alkyl, phenyl-lower-alkyl, cyano-lower-alkyl, carbo-lower-alkoxy-lower-alkyl, carboxamido-lower-alkyl or divalent-lower-alkylene can also be prepared by reacting the corresponding compounds were $R_7$ is hydrogen with a strong base, for example an alkali metal hydride or an alkali metal amide, in an inert organic solvent, for example dimethylsulfoxide, dioxane, dimethylformamide, tetrahydrofuran or dibutyl ether, and reacting the resulting salt with an appropriate alkylating agent, $R_7X$, where X is the anion of a strong mineral acid, for example a hydrogen halide or sulfuric acid, and $R_7$ has the meanings given above. The reaction takes place at a temperature in the range from 15° to about 70° C. and is preferably carried out in dimethyl sulfoxide. The same compounds where $R_7$ is 2-cyanoethyl, 2-(carbo-lower-alkoxy)-ethyl or 2-carboxamidoethyl are prepared by reaction of the compounds of Formula II where $R_7$ is hydrogen with acrylonitrile, an acrylic ester or acrylamide, respectively, in the presence of a strong base, for example benzyltrimethylammonium hydroxide. The reaction is carried out in an inert organic solvent, for example dioxane, diethyl ether, tetrahydrofuran, and the like. The reaction generally takes place at room temperature.

The compounds of Formula I where $R_1$ and $R_2$ are each hydrogen can also be prepared by reduction with one molar equivalent of diisobutyl aluminum hydride (DIBAL) of the compounds of Formula II, and oxidation with oxygen of the resulting cyclopenta[c]pyrrole-4-aldimide having the Formula XX without isolation of the latter. The method is illustrated by the following reaction sequence:

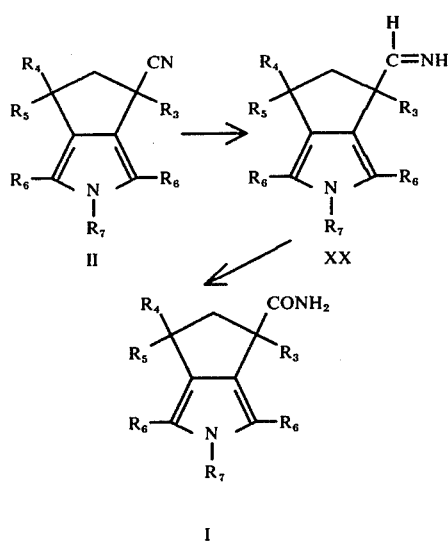

The compounds of Formula XX can also be converted to the final products of Formula I where $R_1$ and $R_2$ are hydrogen and X is O by reacting the aldimide of Formula XX with a peracid, e.g. performic, peracetic or perbenzoic acid, to produce an oxaziridine having the Formula XXI, which on thermal or photochemical decomposition by irradiation with light affords the compounds of Formula I. The method is represented by the reaction sequence:

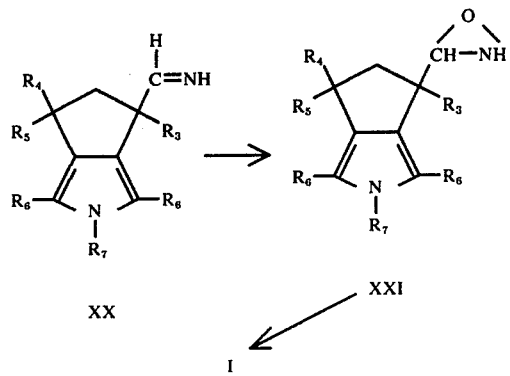

where $R_3$, $R_4$, $R_5$, $R_6$ and $R_7$ have the meanings given above.

Still another method for converting the carbonitriles of Formula II to the carboxamides of Formula I where $R_1$ and $R_2$ are hydrogen and X is O comprises oxidizing the carbonitrile with peroxide, e.g. hydrogen peroxide, in a basic medium, e.g. in the presence of an alkali metal hydroxide, and decomposition of the resulting perimidate of Formula XXII by heating the reaction medium. A preferred solvent is acetone. The method is represented by the reaction sequence:

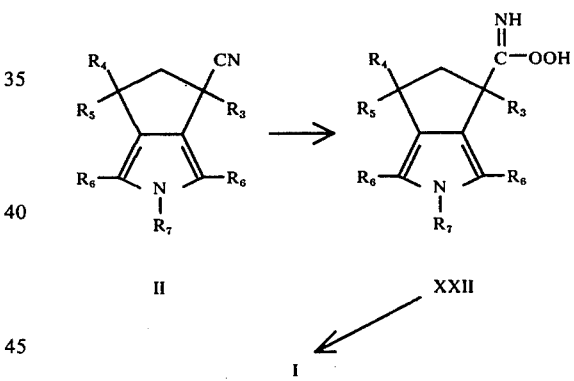

where $R_3$, $R_4$, $R_5$, $R_6$ and $R_7$ have the meanings given above.

The compounds of Formula II, wherein $R_3$, $R_4$ and $R_5$ are each methyl, and each $R_6$ group is the same or different hydrogen, phenyl-lower-alkyl or lower-alkyl, can also be prepared by reaction of a 5,6-dihydro-1H-furo[3,4-c]pyrrole having the Formula XXIII with cyanide in glacial acetic acid with or without added trifluoroacetic acid. The compounds of Formula XXIII are in turn prepared by reaction of a 1,2-di-$R_6$CO-1,2-diacetylethane of Formula XIV with an amine, $R_7NH_2$, and reaction of the resulting 2,5-di-$R_6$-3,4-diacetylpyrrole of Formula XXIV with a methyl magnesium halide. The latter reaction affords the compounds of Formula XXIII directly. The overall method is illustrated by the following reaction sequence where $R_6$ and $R_7$ have the meanings given above.

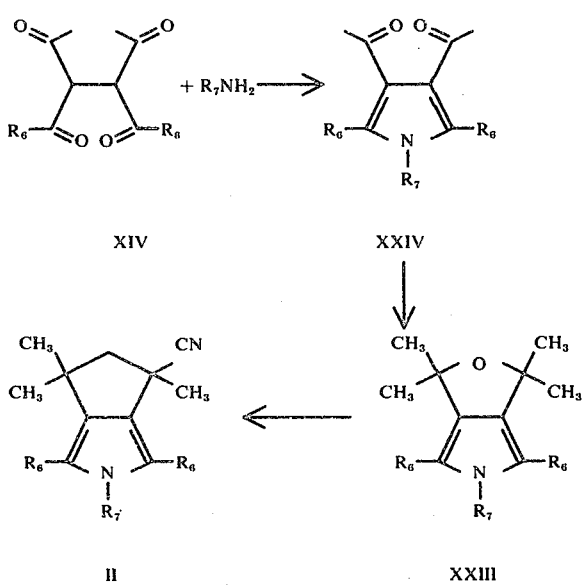

With the exception of the compounds of Formula V, whose method of preparation has been described, all the other starting materials herein are well-known groups of compounds, and many are commercially available.

The novel compounds of the instant invention are the compounds of Formulas I and II and the acid-addition salts of the former in which $R_7$ is a basic, salt-forming group such as di-lower-alkylamino-lower-alkyl, morpholino-lower-alkyl, 1-pyrrolidyl-lower-alkyl, 1-piperidyl-lower-alkyl or a basic heterocyclic group such as pyridyl. The compounds of Formula I in free base form are converted to the acid-addition salt form by interaction of the base with an acid in an orgaic solvent and isolating the salt directly or by concentration of the solution. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the original base and all of their acid-addition salts are readily interconvertible.

In standard biological test procedures, described generally by Shay et al., Gastroenterology 5, 43 (1945) and 26, 906 (1954), the compounds of Formula I have been found to possess anti-secretory and anti-ulcer activity and are thus useful as anti-secretory and anti-ulcer agents. Anti-secretory activity was determined in male albino Wistar rats weighing approximately 180 g. using the test procedure described as follows: the rats were divided into medicated groups of at least five rats each and control groups of ten rats. The rats were medicated orally once daily for two days prior to stomach ligation and once again immediately following ligation. All drugs were administered as the free base, and control rats received only the vehicle of medication. The rats were housed individually in wire cages, and food was withdrawn forty-eight hours prior to surgery, and water was withdrawn at the time of surgery. Laparotomy was performed under light ether anesthesia, the pyloric-duodenal junction was ligated, and the wound was closed with metal clips and sprayed with a protective surgical dressing. Five hours following surgery, the rats were sacrificed, the stomach was removed, and the gastric juice collected. The gastric fluid was centrifuged, and total volume, color, and volume of solids were recorded. The pH of the gastric fluid was then determined on a Beckman pH meter, and the "free" and "total" acid was determined from an aliquot of the gastric fluid by titrating with O.1N sodium hydroxide against Toepfers reagent and phenolphthalein, respectively. The difference between the average amount of "free" acid (expressed as milliequivalents of hydrochloric acid per liter of gastric fluid) of the medicated and control groups was expressed as percent gastric secretory change.

The anti-ulcer activity of the compounds was determined using the reserpine-induced anti-ulcer test method which is described briefly as follows: male, albino, Sprague-Dawley rats, weighing approximately 300 g., were divided into medicated and control groups of at least five rats each, and one positive control group of five rats medicated with a known drug at the active dose was run with each experiment. The rats were medicated 48, 24, and 1 hour before receiving an injection of reserpine. All test drugs were administered orally in terms of base, and the control rats received only the vehicle of medication. The rats were housed individually in wire cages, and food was withdrawn twenty-four hours prior to injection of reserpine, while water was allowed ad libitum. One hour following the third medication, 5.0 mg. of reserpine per kilogram of body weight in a concentration of 5 mg./ml. was injected intramuscularly in each rat. Eighteen hours after injection the rats were sacrificed, their stomachs removed, opended along the greater curvature, rinsed in warm saline, and pinned to a cork board for gross observation. The stomachs were examined for the number and size of ulcerations located in the glandular portion of the stomach with the acid of a 1 millimeter grid ocular with a 10x dissecting microscope. The degree of ulceration was arbitrarily graded according to the number and size of the ulcers as follows:

$0 < 1$ mm.$^2$ 1 point
$1 < 3$ mm.$^2$ 2 points
$\leqslant 3$ mm.$^2$ 5 points.

The points were added together and divided by the number of rats in each group to give an ulcer score, and the difference in the mean scores of the medicated and control group was expressed as percent inhibition of ulceration.

The compounds of Formula I were thus found to inhibit secretion of gastric fluids and to inhibit reserpine-induced stomach ulceration when administered in a dose range of from around 10 mg./kg. to around 200 mg./kg. The compounds are preferably administered orally, and the amount of a particular compound to be administered, either alone or as the essential active ingredient in a formulation, will range from about 10 to about 200 mg./kg.

The actual determination of the numerical biological data definitive for a particular compound of Formula I is readily determined by standard test procedures by technicians versed in pharmacological test procedures without the need for any extensive experimentation.

The compounds of Formula I can be prepared for use by incorporation in unit dosage form as tablets or capsules for oral administration either along or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

I. INTERMEDIATES

A. Intermediates of Formula V:

EXAMPLE 1

A mixture of 57 g. (0.5 mole) of 2,5-hexanedione and 43.5 g. (0.56 mole) of 40% aqueous methylamine in 250 ml. of benzene was refluxed under a Dean-Stark trap until no more water was carried over, and the resulting solution was taken to dryness. The residual oily material was distilled in vacuo to give 34 g. of 1,2,5-trimethylpyrrole, b.p. 58°–59° C./ 20 mm.

Following a procedure similar to that described in Example 1, using an appropriate alkanedione of Formula III and an appropriate amine, $R_7NH_2$, the following 1-$R_7$-2,5-di-$R_6$-substituted-pyrroles of Formula V were prepared. Here and elsewhere throughout this specification in subsequent tables, the weights of the starting materials and products are given in grams in the appropriate columns headed "Wt. ", and melting points or boiling points of the final products, together with the solvent of recrystallization (for solids) or pressure in mm. of mercury (at the boiling point for liquids) as the case may be, are given in the last column. Where weights of only one of several reactants are given, the weights of such other reactants can be calculated on a proportionate molar basis from the amounts used in the example referred to for the preparative procedure employed. Moreover, in each of the tables which follow, both $R_6$ groups in each of the products are identical unless specifically noted otherwise. Where the $R_6$ groups are different, the substituents represented by the $R_6$ moieties are designated (1) and (3) to indicate location of the substituents at the 1- and 3-positions, respectively, of the cyclopenta[c]pyrrole nucleus.

In some instances, the products were neither characterized nor purified, either by distillation or recrystallization, but rather were used directly in the next step as isolated from the reaction mixture.

Table 1a

| Example | $R_6$ | $R_7$ | Wt. III | Wt. V | m.p. (° C.)/Solvent or b.p. (° C.)/mm.Hg. |
|---|---|---|---|---|---|
| 1A | $CH_3$ | —$(CH_2)_6$— | 114 | 66 | 102–105/cyclohexane |
| 1B | $CH_3$ | $CH_2CH_2C_6H_5$ | 57 | 91 | 163–165/14–20 |
| 1C | $CH_3$ | 4-$NH_2SO_2C_6H_4$ | 114 | 118 | 157–158.5/methanol |
| 1D | $CH_3$ | $C_6H_5$ | 114 | 152 | 155–160/15 |
| 1E | $CH_3$ | $C_2H_5$ | 57 | 95 | 75–78/15–20 |
| 1F | $CH_3$ | $C_3H_7$ | 114 | 103 | 80–82/15–20 |
| 1G | $CH_3$ | 4-$CH_3OC_6H_4$ | 114 | 162 | 104–105/0.01 |
| 1H | $CH_3$ | 4-$CH_3C_6H_4$ | 114 | 143 | 65–76/0.05 |
| 1J | $CH_3$ | 4-$ClC_6H_4$ | 114 | 169 | 104/0.04 |
| 1K | $CH_3$ | 3-$ClC_6H_4$ | 114 | 188 | 96–98/0.05 |
| 1L | $CH_3$ | 2-pyridyl | 114 | 132 | 74–90/0.03 |
| 1M | $CH_3$ | 3-$CH_3C_6H_4$ | 114 | 158 | 78–80/0.05 |
| 1N | $CH_3$ | 2-$ClC_6H_4$ | 114 | 174 | 84–94/0.05 |
| 1P | $CH_3$ | 2-$CH_3C_6H_4$ | 114 | 143 | 117–119/0.05 |
| 1Q | $CH_3$ | 4-$FC_6H_4$ | 114 | 155 | 116–120/15 |
| 1R | $CH_3$ | 4-$(CH_3)_2NC_6H_4$ | 57 | 79 | methanol |
| 1S | $CH_3$ | 4-$HOC_6H_4$ | 114 | 161 | 121–138/0.5–0.05 m.p. 102–105 |
| 1T | $CH_3$ | 4-$CH_3CONHC_6H_4$ | 114 | 169 | methanol |
| 1U | $CH_3$ | iso-$C_3H_7$ | 57 | 49.7 | 80–82.5/17 |
| 1V | $CH_3$ | $CH_2CH_2OC_2H_5$ | 62.7 | 67.1 | 105–108.5/760 $n_D^{26}$ 1.4845 |
| 1W | $CH_3$ | $CH_2COOC_2H_5$ | 62.7 | 73.9 | 125–127/13 $n_D^{23}$ 1.4903 |
| 1X | $CH_3$ | cyclohexyl | 114 | 132 | 83–89/0.02 |
| 1Y | $C_2H_5$ | $C_6H_5$ | 7.6 | 12.3 | Dark oil |
| 1Z | $CH_3$ | cyclopropyl | 50 | 52.8 | 36–39/0.3 |
| 1AA | $CH_3$ | cyclopentyl | 57.1 | 66.7 | 63–72/0.03 $n_D^{25}$ 1.5210 |
| 1AB | $CH_3$ | $CH_2CH_2N(CH_3)_2$ | 46.3 | 58.5 | 48/0.03 $n_D^{25}$ 1.4922 |
| 1AC | $CH_3$ | $CH_2CH_2N(CH_2CH_2)_2O$ | 22.8 | 37.6 | 89–104/0.05 $n_D^{25}$ 1.5167 |
| 1AD | $CH_3$ | $CH_2CH_2CH_2OH$ | 34.2 | 38.5 | 83–96/0.05 |
| 1AE | $CH_3$ | cyclobutyl | 21.2 | 18.2 | 50–55/0.2 $n_D^{25}$ 1.5202 |
| 1AF | $CH_3$ | 4-$HOOCC_6H_4$ | 114 | 106 | m.p. 202–204 |
| 1AG | $CH_3$ | 4-$O_2NC_6H_4$ | 114 | 103 | m.p. 146–149 |
| 1AH | $CH_3$ | sec.-$C_4H_9$ | 55.6 | 55.7 | 90–94/21 |
| 1AJ | $CH_3$ | iso-$C_4H_9$ | 68.4 | 82.4 | 94–95/22 |
| 1AK | $CH_3$ | 3,4—$\overline{OC(CH_3)_2OC_6H_3}$ | 5.7 | 10.4 | m.p. 100–111 |
| 1AL | $CH_3$ | 4-$C_2H_5OC_6H_4$ | 34.2 | 51.2 | 101–107/0.4 |
| 1AM | $CH_3$ | 3-$CF_3C_6H_4$ | 22.8 | 42.8 | 41–55/0.07 $n_D^{24}$ 1.5065 |
| 1AN | $CH_3$ | $CH_2C\equiv CH$ | 20.5 | 18.8 | 96.5–100/20 |
| 1AP | $CH_3$ | 3,5-$(CH_3O)_2C_6H_3$ | 23.5 | 27.1 | 123–129/0.4 |
| 1AQ | $CH_3$ | $CH_2CH_2F$ | 27.4 | 28.6 | 85–89/14 |

Table 1a-continued

| Example | $R_6$ | $R_7$ | Wt. III | Wt. V | m.p. (° C.)/Solvent or b.p. (° C.)/mm.Hg. |
|---|---|---|---|---|---|
| 1AR | $CH_3$ | $CH_2CH_2Cl$ | 57 | 64.0 | 93–108/14 |

Following a procedure similar to that described in Example 1, using an appropriate alkanedione of Formula III and an appropriate amine, $R_7NH_2$, in refluxing benzene or toluene, the following compounds of Formula V are prepared.

Table 1b

| Example | $R_6$ | $R_7$ |
|---|---|---|
| 1AS | $CH_3$ | 3-pyridyl |
| 1AT | $CH_3$ | $CH_2CH_2SC_2H_5$ |
| 1AU | $CH_3$ | $4-BrC_6H_4$ |
| 1AV | $CH_3$ | $2,4,6-Cl_3C_6H_2$ |
| 1AW | $CH_3$ | $2-Cl-4-CH_3C_6H_3$ |
| 1AX | $CH_3$ | $3,4-OCH_2OC_6H_3$ |
| 1AY | $CH_3$ | $4-CF_3C_6H_4$ |
| 1AZ | $CH_3$ | $2,4,6-(CH_3)_3C_6H_2$ |
| 1BA | $C_3H_7$ | $C_6H_5$ |
| 1BB | iso-$C_3H_7$ | $C_6H_5$ |
| 1BC | $C_4H_9$ | $C_6H_5$ |
| 1BD | $CH_3$ | cyclohexyl-$CH_2$ |
| 1BE | $CH_3$ | $CH_2CH_2-N(CH_2)_4$ |
| 1BF | $CH_3$ | $CH_2CH_2-N(CH_2)_5$ |
| 1BG | $CH_3$ | 2-thienyl |
| 1BH | $CH_3$ | $3-H_2NOO-C_6H_4$ |
| 1BJ | $CH_3$ | $3-CH_3SC_6H_4$ |
| 1BK | $C_6H_5CH_2$ | $C_6H_5$ |
| 1BL | $CH_3$ | 9-acridinyl |
| 1BM | $CH_3$ | 4-(2,1,3-benzothiazolyl) |
| 1BN | $CH_3$ | 2-benzothiazolyl |
| 1BP | $CH_3$ | 3-carbazolyl |
| 1BQ | $CH_3$ | 2-benzoxazolyl |
| 1BR | $CH_3$ | 2-purinyl |
| 1BS | $CH_3$ | 6-purinyl |
| 1BT | $CH_3$ | 2-pyrazinyl |
| 1BU | $CH_3$ | 4-pyrimidinyl |
| 1BV | $CH_3$ | 2-thiazolyl |
| 1BW | $CH_3$ | 3-pyrazolyl |
| 1BX | $CH_3$ | 2-pyrimidinyl |
| 1BY | $CH_3$ | 6-pyrimidinyl |
| 1BZ | $CH_3$ | 2-benzimidazolyl |
| 1CA | $CH_3$ | 2-benzothiazolyl |
| 1CB | $CH_3$ | 5-indazolyl |
| 1CC | $CH_3$ | 6-indazolyl |
| 1CD | $CH_3$ | 7-indazolyl |
| 1CE | $CH_3$ | 5-isoquinolinyl |
| 1CF | $CH_3$ | 3-pyridazinyl |
| 1CG | $CH_3$ | 2-thiadiazolyl |
| 1CH | $CH_3$ | 5-tetrazolyl |
| 1CJ | $CH_3$ | 2-thiazolinyl |
| 1CK | $CH_3$ | 3-(1,2,4-triazinyl) |
| 1CL | $CH_3$ | 3-(1,2,4-triazolyl) |

B. Intermediates of Formula II

EXAMPLE 2

A mixture of 260 g. (2.4 moles) of 1,2,5-trimethylpyrrole, 280 g. (4.8 moles) of acetone, 185 g. (2.4 moles) of ammonium acetate and 320 g. (4.8 moles) of potassium cyanide in one liter of glacial acetic acid was stirred and heated under reflux under a nitrogen atmosphere for 2 days. The mixture was cooled to about 60° C., poured into an ice-water mixture with stirring, and the solid which separated was dissolved in 3 liters of diethyl ether, the solution washed with water and saturated bicarbonate, and taken to dryness to give 412 g. of crude product which was recrystallized from hexane to give 151 g. of 2,4,5,6-tetrahydro-1,2,3,4,6,6-hexamethylcyclopenta[c]pyrrole-4-carbonitrile, m.p. 123°–125° C.

EXAMPLE 3

To a solution of 220 g. (4.1 moles) of ammonium chloride, 232 g. (4.0 moles) of acetone and 600 ml. of diethyl ether was added with cooling and vigorous stirring a solution of 280 g. (4.3 moles) of potassium cyanide in 440 ml. of water. The cooling bath was then removed, the mixture stirred at room temperature overnight, the organic phase separated, and the aqueous phase washed with diethyl ether. The combined organic fractions were dried and taken to dryness to give a yellow liquid which was distilled in vacuo to give 162 g. of 2-amino-2-methylpropionitrile, b.p. 61°–62° C./20 mm.

A mixture of 119 g. (1.42 moles) of 2-amino-2-methylpropionitrile, 155 g. (1.36 moles) of 2,5-hexanedione and 500 ml. of glacial acetic acid was refluxed under nitrogen for about four days, and the reaction mixture was evaporated to dryness. (With an equimolar amount of trifluoroacetic acid present, the reaction time can be decreased to three hours). The residue was taken up in diethyl ether, washed repeatedly with dilute hydrochloric acid, water, then dilute aqueous sodium bicarbonate, dried over sodium sulfate, and taken to dryness to give a brown solid which was recrystallized from acetonitrile to give about 33 g. of 2,4,5,6-tetrahydro-1,3,4,6,6-pentamethylcyclopenta[c]pyrrole-4-carbonitrile, m.p. 130°–140° C., which on sublimation afforded 26.7 g. of the compound having m.p. 150.5°–152.5° C.

EXAMPLE 4

A mixture of 27.2 g. (0.1 mole) of 1,1′-hexamethylenebis[2,5-dimethylpyrrole] described in Example 1A, 33.6 g. (0.4 mole) of 2-amino-2-methylpropionitrile, 50 g. (0.4 mole) of trifluoroacetic acid and 200 ml. of glacial acetic acid was heated under reflux for about two and one half hours, then cooled, poured into water, and the gummy solid which separated was filtered, washed with water, and recrystallized from hot acetonitrile to give 14.3 g. of 2,2′-hexamethylenebis[2,4,5,6-tetrahydro-1,3,4,6,6-pentamethylcyclopenta[c]pyrrole-4-carbonitrile], m.p. 227.5°–229.5° C.

Following a procedure similar to that described in Example 4, using an appropriate 1-$R_7$-2,5-di-$R_6$-substituted pyrrole of Formula V described above, the following 2,4,5,6-tetrahydrocyclopenta[c]pyrrole-4-carbonitriles of Formula II were prepared where, in each instance, $R_3$, $R_4$ and $R_5$ are $CH_3$.

Table 4a

| Example | $R_6$ | $R_7$ | Wt. V | Wt. II | m.p. (° C.)/Solvent |
|---|---|---|---|---|---|
| 4A | $CH_3$ | $CH_2CH_2C_6H_5$ | 40 | 40 | 92–94/methanol |
| 4B | $CH_3$ | $4-NH_2SO_2C_6H_4$ | 57 | 57 | 255–257/ethanol |
| 4C | $CH_3$ | $C_6H_5$ | 17.1 | 24.5 | 115–117 |
| 4D | $CH_3$ | $C_2H_5$ | 72 | 42 | methanol |

Table 4a-continued

| Example | $R_6$ | $R_7$ | Wt. V | Wt. II | m.p. (° C.)/Solvent |
|---|---|---|---|---|---|
| 4E | $CH_3$ | $C_3H_7$ | 64 | 64 | 75–77/hexane |
| 4F | $CH_3$ | $4-CH_3OC_6H_4$ | 162 | 74 | isopropanol |
| 4G | $CH_3$ | $4-CH_3C_6H_4$ | 93 | 140 | |
| 4H | $CH_3$ | $4-ClC_6H_4$ | 147 | 125 | 136–139/isopropanol |
| 4J | $CH_3$ | $3-ClC_6H_4$ | 106.5 | 81.4 | isopropanol/methanol |
| 4K | $CH_3$ | 2-pyridyl | 93 | 87 | |
| 4L | $CH_3$ | $3-CH_3C_6H_4$ | 100 | 95 | acetonitrile |
| 4M | $CH_3$ | $2-ClC_6H_4$ | 92 | 117 | |
| 4N | $CH_3$ | $2-CH_3C_6H_4$ | 93 | 102.5 | b.p. 139–142/0.25–30 |
| 4P | $CH_3$ | $4-FC_6H_4$ | 94 | 88 | isopropanol |
| 4Q | $CH_3$ | $4-(CH_3)_2NC_6H_4$ | 57 | 54 | methanol |
| 4R | $CH_3$ | $4-HOC_6H_4$ | 155 | 157 | |
| 4S | $CH_3$ | $4-CH_3CONHC_6H_4$ | 68 | 47 | acetonitrile |
| 4T | $CH_3$ | iso-$C_3H_7$ | 49.7 | 25.6 | 76–80/hexane |
| 4U | $CH_3$ | $CH_2CH_2OC_2H_5$ | 66.1 | 103.1 | |
| 4V | $CH_3$ | $CH_2COOC_2H_5$ | 72.4 | 55.3 | 60–62/cyclohexane |
| 4W | $CH_3$ | cyclohexyl | 88 | 81 | isopropanol |
| 4X | $CH_3$ | cyclopropyl | 27.4 | 24.7 | isopropanol |
| 4Y | $CH_3$ | cyclopentyl | 32.8 | 38.2 | 98–102/isopropanol-$H_2O$ |
| 4Z | $CH_3$ | $CH_2CH_2N(C_2H_5)_2$ | 8.4 | 1.3 | b.p. 115/0.05; $n_D^{25}$ 1.5095 |
| 4AA | $CH_3$ | $CH_2CH_2N(CH_2CH_2)_2O$ | 20.8 | 9.4 | 103–105/hexane |
| 4AB | $CH_3$ | $CH_2CH_2CH_2OH$ | 30.6 | 1.8 | 100–101/pentane |
| 4AC | $CH_3$ | cyclobutyl | 18.2 | 9.5 | 95–98 |
| 4AD | $CH_3$ | $4-O_2NC_6H_4$ | 20.8 | 12.5 | 206–208.5 |
| 4AE | $CH_3$ | sec.-$C_4H_9$ | 30.3 | 40.0 | b.p. 98/0.15–104/0.35 |
| 4AF | $CH_3$ | iso-$C_4H_9$ | 15.1 | 18.6 | b.p. 102–107/0.25 |
| 4AG | $CH_3$ | $3,4-OC(CH_3)_2OC_6H_3$ | 9.75 | 5.1 | 158–161 |
| 4AH | $CH_3$ | $4-C_2H_5OC_6H_4$ | 43.0 | 35.3 | 138–140/ether-pentane |
| 4AJ | $CH_3$ | $3-CF_3C_6H_4$ | 42.5 | 6.9 | b.p. 140–155/0.08 |
| 4AK | $CH_3$ | $CH_2C{\equiv}CH$ | 18.8 | 22.9 | 106–106.5/cyclohexane |
| 4AL | $CH_3$ | $3,5-(CH_3O)_2C_6H_3$ | 23.1 | 23.4 | |
| 4AM | $CH_3$ | $CH_2CH_2F$ | 28.6 | 17.7 | 94–95/cyclohexane |
| 4AN | $CH_3$ | $CH_2CH_2Cl$ | 60 | 54.9 | 101–103/isopropanol |
| 4AP | $C_2H_5$ | $C_6H_5$ | 5.9 | 11.7 | viscous oil |

Following a procedure similar to that described in Example 4, using an appropriate 1-$R_7$-2,5-di-$R_6$-substituted-pyrrole of Formula V described above and 2-amino-2-methylpropionitrile, the following 2,4,5,6-tetrahydrocyclopenta[c]pyrrole-4-carbonitriles of Formula II are prepared where, in each instance, $R_3$, $R_4$ and $R_5$ are $CH_3$.

Table 4b

| Example | $R_6$ | $R_7$ |
|---|---|---|
| 4AQ | $CH_3$ | 3-pyridyl |
| 4AR | $CH_3$ | $CH_2CH_2SC_2H_5$ |
| 4AS | $CH_3$ | $4-BrC_6H_4$ |
| 4AT | $CH_3$ | $2,4,6-Cl_3C_6H_2$ |
| 4AU | $CH_3$ | $2-Cl-4-CH_3C_6H_3$ |
| 4AV | $CH_3$ | $3,4-OCH_2OC_6H_3$ |
| 4AW | $CH_3$ | $4-CF_3C_6H_4$ |
| 4AX | $CH_3$ | $2,4,6-(CH_3)_3C_6H_2$ |
| 4AY | $C_3H_7$ | $C_6H_5$ |
| 4AZ | iso-$C_3H_7$ | $C_6H_5$ |
| 4BA | $C_4H_9$ | $C_6H_5$ |
| 4BB | $CH_3$ | cyclohexyl-$CH_2$ |
| 4BC | $CH_3$ | $CH_2CH_2N(CH_2)_4$ |
| 4BD | $CH_3$ | $CH_2CH_2N(CH_2)_5$ |
| 4BE | $CH_3$ | 2-thienyl |
| 4BF | $CH_3$ | $4-HOOCC_6H_4$ |
| 4BG | $CH_3$ | $3-H_2NCOC_6H_4$ |
| 4BH | $CH_3$ | $3-CH_3SC_6H_4$ |
| 4BJ | $C_6H_5CH_2$ | $C_6H_5$ |
| 4BK | $CH_3$ | 9-acridinyl |
| 4BL | $CH_3$ | 4-(2,1,3-benzothiadiazolyl) |
| 4BM | $CH_3$ | 2-benzothiazolyl |
| 4BN | $CH_3$ | 3-carbazolyl |
| 4BP | $CH_3$ | 2-benzoxazolyl |
| 4BQ | $CH_3$ | 2-purinyl |
| 4BR | $CH_3$ | 6-purinyl |
| 4BS | $CH_3$ | 2-pyrazinyl |
| 4BT | $CH_3$ | 4-pyrimidinyl |
| 4BU | $CH_3$ | 2-thiazolyl |
| 4BV | $CH_3$ | 3-pyrazolyl |
| 4BW | $CH_3$ | 2-pyrimidinyl |
| 4BX | $CH_3$ | 6-pyrimidinyl |
| 4BY | $CH_3$ | 2-benzimidazolyl |

Table 4b-continued

| Example | $R_6$ | $R_7$ |
|---|---|---|
| 4BZ | $CH_3$ | 2-benzothiazolyl |
| 4CA | $CH_3$ | 5-indazolyl |
| 4CB | $CH_3$ | 6-indazolyl |
| 4CC | $CH_3$ | 7-indazolyl |
| 4CD | $CH_3$ | 5-isoquinolinyl |
| 4CE | $CH_3$ | 3-pyridazinyl |
| 4CF | $CH_3$ | 2-thiadiazolyl |
| 4CG | $CH_3$ | 5-tetrazolyl |
| 4CH | $CH_3$ | 2-thiazolinyl |
| 4CJ | $CH_3$ | 3-(1,2,4-triazinyl) |
| 4CK | $CH_3$ | 3-(1,2,4-triazolyl) |

EXAMPLE 5

In a separate run following the procedure described above in Example 4, in which approximately a 1 kg. batch of 2-phenyl-2,4,5,6-tetrahydro-1,3,4,6,6-pentamethylcyclopenta[c]pyrrole-4-carbonitrile described above in Example 4C was prepared, a sample of a by-product weighing approximately 100 g. was isolated, and the latter was recrystallized from toluene to give 69 g. of 3,3,3',3',4,4',6,6'-octamethyl-5,5'-diphenyl-1,1'-spirobis(cyclopenta[4,5-c]pyrrole), m.p. 210°–212° C.

The latter, on reaction with two molar equivalents each of acetone and ammonium acetate and four molar equivalents of potassium cyanide in glacial acetic acid affords 2-phenyl-2,4,5,6-tetrahydro-1,3,4,6,6-pentamethylcyclopenta[c]pyrrole-4-carbonitrile, identical with that described in Example 4C above.

EXAMPLE 6

A mixture of 9.5 g. (0.1 mole) of 2,5-dimethylpyrrole and a suspension of 7 g. (0.1 mole) of potassium cyanide in 9 ml. of water and 18 ml. of acetone was stirred vigorously with external cooling and neutralized first with about 10 ml. of concentrated hydrochloric acid and then acidified with an additional 3 ml. of concentrated hydrochloric acid. The mixture was then heated at 50° C. for five hours and poured into 500 ml. of water. The solid gummy material which separated was collected, washed with water, then taken into diethyl ether, and the organic solution washed with water, then sodium bicarbonate, then brine, dried and taken to dryness to give a solid material, which was recrystallized from cyclohexane to give two crops totaling 5.0 g. of 3,3,3',3',4,4',6,6'-octamethyl-1,1'-spirobis(cyclopenta[4,5-c]pyrrole), m.p. 184°–190° C. and 183°–188° C.

The latter (2.2 g., 0.007 mole), together with 0.83 g. (0.014 mole) of acetone, 1.1 g. (0.014 mole) of ammonium acetate and 1.9 g. (0.028 mole) of potassium cyanide in 10 ml. of glacial acetic acid was heated under reflux under a nitrogen atmosphere for 18 hours. The mixture was then poured into water, and the solid which separated was dissolved in diethyl ether, washed first with water, then with sodium bicarbonate, then with saturated brine, dried and the solution taken to dryness. The residual solid was triturated with cyclohexane to give 2.1 g. of 2,4,5,6-tetrahydro-1,3,4,6,6-pentamethylcyclopenta[c]pyrrole-4-carbonitrile, m.p. 146°–150° C., identical with the material described above in Example 3.

EXAMPLE 7

To a solution prepared by heating 23.2 g. (0.55 mole) of a 67% mineral oil dispersion of sodium hydride in 200 ml. of anhydrous dimethylsulfoxide was added 50.5 g. (0.25 mole) of the 2,4,5,6-tetrahydro-1,3,4,6,6-pentamethylcyclopenta[c]pyrrole-4-carbonitrile described above in Example 3. The mixture was stirred under nitrogen for about two hours, cooled to 15° C., and treated with 39.5 g. (0.25 mole) of 3-chloro-N,N-dimethylpropylamine hydrochloride. When the foaming had subsided, the mixture was stirred at room temperature overnight, poured into water, and the gummy solid which separated was taken into diethyl ether and the solution washed first with water, then with saturated brine, dried and taken to dryness to give 69 g. of a solid which was recrystallized once from hexane and once from isopropanol to give 29 g of 2-[3-(di-methylamino)propyl]-2,4,5,6-tetrahydro-1,3,4,6,6-pentamethylcyclopenta[c]pyrrole-4-carbonitrile, m.p. 90.5°–91.0° C.

Following a procedure similar to that described in Example 7, using an appropriate 2,4,5,6-tetrahydrocyclopenta[c]pyrrole-4-carbonitrile of Formula II where $R_7$ is hydrogen, the following 2,4,5,6-tetrahydro-1,3,4,6,6-pentamethylcyclopenta[c]pyrrole-4-carbonitriles of Formula II were prepared where, in each instance, $R_3$, $R_4$, $R_5$ and $R_6$ are each $CH_3$. (The abbreviations S.M. and Prod. represent starting material and product, respectively).

Table 7

| Example | $R_7$ | Wt.II (S.M.) | Wt.II (Prod.) | m.p.(° C.)/ Solvent |
|---|---|---|---|---|
| 7A | $CH_2C_6H_5$ | 50.5 | 49 | 86–88/methanol |
| 7B | $C_4H_9$ | 40.4 | 34.3 | 53–55/pentane |
| 7C | cyclopropyl-$CH_2$ | 40.4 | 33.2 | 90–92/pentane |

EXAMPLE 8

To a solution of 20.2 g. (0.1 mole) of 2,4,5,6-tetrahydro-1,3,4,6,6-pentamethylcyclopenta[c]pyrrole-4-carbonitrile, described above in Example 3, in 100 ml. of dioxane was added 5.6 g. (0.11 mole) of acrylonitrile and 6.4 ml. of a 35% solution of benzyltrimethyl ammonium hydroxide (Triton B) in methanol, and the mixture was stirred at room temperature under nitrogen overnight. The mixture was then poured into ice water, acidified with dilute hydrochloric acid, and the solid which separated was washed with water, dried and recrystallized from ethanol to give 14.8 g. of 2-(2-cyanoethyl)-2,4,5,6-tetrahydro-1,3,4,6,6-pentamethylcyclopenta[c]pyrrole-4-carbonitrile, m.p. 169°–170° C.

EXAMPLE 9

A solution of 27.8 g. (0.1 mole) of 2-phenyl-2,4,5,6-tetrahydro-1,3,4,6,6-pentamethylcyclopenta[c]pyrrole-4-carbonitrile (described above in Example 4C) dissolved in 400 ml. of diethyl ether was cooled to 0° C. and treated dropwise with stirring with a solution of 81.0 g. (0.6 mole) of sulfuryl chloride in 100 ml. of diethyl ether, and the solution was stirred at room temperature for several hours. The mixture was then poured into ice water, extracted with ether, and the combined ether extracts dried and taken to dryness to give 42 g. of a gummy solid which was triturated with hot diethyl ether to give 23.5 g. of 2-phenyl-2,4,5,6-tetrahydro-1,3-bis-dichloromethyl-4,6,6-trimethylcyclopenta[c]pyrrole-4-carbonitrile, m.p. 186°–188.5° C.

A solution of the latter (36.0 g., 0.087 mole) dissolved in 400 ml. of 50% aqueous ethanol was refluxed for one hour and then cooled. The solid which separated was collected and dissolved in chloroform, and the organic solution washed once with water and once with saturated sodium bicarbonate, dried, and taken to dryness to give 28 g. of crude material which was recrystallized from isopropanol to give 19.8 g. of 2-phenyl-2,4,5,6-tetrahydro-1,3-diformyl-4,6,6-trimethylcyclopenta[c]pyrrole-4-carbonitrile, m.p. 135°–136.5° C.

EXAMPLE 9A

Following a procedure similar to that described in Example 9, 1 kg. (3.6 moles) of 2-phenyl-2,4,5,6-tetrahydro-1,3,4,6,6-pentamethylcyclopenta[c]pyrrole-4-carbonitrile, described in Example 4C, in 12.5 liters of carbon tetrachloride was reacted with 585 ml. (7.2 moles) of sulfuryl chloride to give 862 g. of 2-phenyl-2,4,5,6-tetrahydro-1,3-bis-chloromethyl-4,6,6-trimethylcyclopenta[c]pyrrole-4-carbonitrile m.p. 123°–126° C. (from cyclohexane). The latter (800 g., 2.5 moles) was hydrolyzed in a solution of 410 g. (5.0 moles) of anhydrous sodium acetate in 8.1 liters of trifluoroacetic acid at a temperature of from 25° C. to 36° C., and the product was recrystallized from isopropanol to give 362 g. of 2-phenyl-2,4,5,6-tetrahydro-3-formyl-1,4,6,6-tetramethylcyclopenta[c]pyrrole-4-carbonitrile m.p. 132–135° C.

The mother liquors were recovered, evaporated to dryness and treated with 90% aqueous sulfuric acid in the manner described in Example 20 below. There was thus obtained 2-phenyl-2,4,5,6-tetrahydro-1-formyl-3,4,6,6-tetramethylcyclopenta[c]pyrrole-4-carboxamide, identical with the compound described in Example 20AZ.

EXAMPLE 10

1-Phenyl-2,5-dimethylpyrrole, described above in Example 1D (124 g., 0.74 mole), in 200 ml. of ethylene dichloride was reacted with 58.4 g. (0.8 mole) of dimethylformamide and 123 g. (0.8 mole) of phosphorus oxychloride in the presence of 550 g. (4.0 moles) of sodium acetate trihydrate in 720 ml. of water using the procedure described in Organic Syntheses, Coll. Vol. 4, page 831 (1963), John Wiley and Sons, New York. The crude product was recrystallized from methanol to give 112.5 g. of 1-phenyl-2,5-dimethyl-3-formylpyrrole, m.p. 89°–91° C.

A suspension of 26.2 g. (0.62 mole) of a 57% mineral oil dispersion of sodium hydride in 200 ml. of dimethylformamide was prepared and treated portionwise with 116 g. (0.59 mole) of diethoxy phosphonoacetonitrile in 100 ml. of dimethylformamide. When the exothermic reaction had subsided, the mixture was treated with a solution of 112.5 g. (0.57 mole) of the above-described 1-phenyl-2,5-dimethyl-3-formylpyrrole in 600 ml. of dimethylformamide. When the reaction had subsided, the reaction mixture was poured into water, filtered, and the solid material recrystallized from methanol to give 61.5 g. of 1-phenyl-2,5-dimethylpyrrole-3-acrylonitrile, m.p. 145°–147.5° C.

The latter (10.0 g., 0.045 mole) dissolved in 250 ml. of methanol was reduced under an initial hydrogen pressure of 50 psi at room temperature over 2 g. of a 10% palladium-on-charcoal catalyst. When reduction was complete, the catalyst was removed by filtration, the filtrate taken to dryness, and the solid residue recrystallized from cyclohexane to give 6.65 g. of 3-(1-phenyl-2,5-dimethyl-3-pyrrole)propionitrile, m.p. 83.5°–85.5° C.

The latter, on refluxing in ethanolic potassium hydroxide and isolation from a slightly acid medium, affords 3-(1-phenyl-2,5-dimethyl-3-pyrrole)propionic acid.

3-(1-Phenyl-2,5-dimethyl-3-pyrrole)propionic acid was also obtained as follows: To a suspension of 9.6 g. (0.2 mole) of a 50% mineral oil dispersion of sodamide in 400 ml. of 1,2-dimethoxyethane was added 49.2 g. (0.22 mole) of ethyl diethoxyphosphonoacetate, and the mixture was stirred at ambient temperature for fifteen minutes, cooled to 0°–5° C. and treated with 39.8 g. (0.2 mole) of 1-phenyl-2,5-dimethyl-3-formylpyrrole. The mixture was stirred for one hour at 35°–40° C., then for ten hours at 0.5° C., poured onto ice and extracted with diethyl ether. The ether extracts, on drying and evaporation to dryness, afforded 48.8 g. of ethyl 3-(1-phenyl-2,5-dimethyl-3-pyrrole)acrylate. Reduction of 42.7 g. (0.16 mole) of the latter in 250 ml. of ethanol over 1 g. of 10% palladium-on-charcoal in a Parr shaker afforded 53 g. of ethyl 3-(1-phenyl-2,5-dimethyl-3-pyrrole)propionate, which on saponification with alkali afforded 3-(1-phenyl-2,5-dimethyl-3-pyrrole)propionic acid.

A mixture of 1 g. (0.004 mole) of the latter in 10 g. of polyphosphoric acid was heated at 95° C. for twelve hours, and then poured into ice/water and extracted with ether. The ether extracts, on washing, drying and evaporation to dryness, afforded a solid which was recrystallized from cyclohexane to give 700 mg. of 4-oxo-1,3-dimethyl-2-phenyl-2,4,5,6-tetrahydrocyclopenta[c]pyrrole, m.p. 71°–73° C.

The latter (2.0 g., 0.0089 mole) was dissolved in tetrahydrofuran, and the solution was treated with a solution of 0.0097 mole of methyl magnesium bromide in tetrahydrofuran and stirred at 0°–5° C. for twelve hours, then at ambient temperature for four hours. The mixture was then partitioned between water and ether and the ether extracts, on washing, drying and evaporation to dryness afforded 4-hydroxy-1,3,4-trimethyl-2-phenyl-2,4,5,6-tetrahydrocyclopenta[c]pyrrole as an oil.

The latter, along with 2.6 g. (0.04 mole) of potassium cyanide and 4 g. (0.04 mole) of potassium acetate, was dissolved in 40 ml. of glacial acetic acid and the solution refluxed for two hours and then partitioned between water and ether. The ether extracts, on washing, drying and evaporation to dryness, afforded an oil which was dissolved in hexane and chromatographed on silica, eluting with hexane. There was thus obtained 500 mg. of 1,3,4-trimethyl-2-phenyl-2,4,5,6-tetrahydrocyclopenta[c]pyrrole-4-carbonitrile as an oil.

EXAMPLE 10A 1,2,5-Trimethylpyrrole (109 g., 1.0 mole) in 250 ml. of ethylene dichloride was reacted with 80 g. (1.1 moles) of dimethylformamide and 169 g. (1.1 moles) of phosphorus oxychloride in the presence of 750 g. (5.5 moles) of sodium acetate trihydrate in one liter of water using the procedure described in Organic Syntheses, Coll. Vol. 4, page 831, (1963) John Wiley and Sons, New York, and the crude product was recrystallized from acetonitrile to give 71.1 g. of 1,2,5-trimethyl-3-formylpyrrole, m.p. 97°–99° C.

A suspension of 9.3 g. (0.22 mole) of a 57% mineral oil dispersion of sodium hydride in 200 ml. of anhydrous 1,2-dimethoxyethane was treated dropwise with 37.5 g. (0.2 mole) of diethoxyphosphonoacetonitrile, and the mixture was stirred until evolution of hydrogen had ceased. The resulting solution was then treated with a solution of 27.4 g. (0.2 mole) of the above 1,2,5-trimethyl-3-formylpyrrole in 250 ml. of 1,2-di-methoxyethane. When the exothermic reaction had subsided, the mixture was heated to 80° C., then allowed to cool to room temperature, diluted with 100 ml. of dimethylformamide, heated to reflux, then cooled and poured into ice water. The solid which separated was collected and recrystallized from methanol to give 14 g. of 1,2,5-trimethylpyrrole-3-acrylonitrile, m.p. 148.5°–150.5° C.

Reduction of the latter with hydrogen over a palladium-on-charcoal catalyst; alkaline saponification of the resulting 3-(1,2,5-trimethyl-3-pyrrole)propionitrile; cyclization of the resulting 3-(1,2,5-trimethyl-3-pyrrole)propionic acid with polyphosphoric acid; reaction of the resulting 4-oxo-1,2,3-trimethyl-2,4,5,6-tetrahydrocyclopenta[c]pyrrole with methyl magnesium bromide; and reaction of the resulting 4-hydroxy-1,2,3,4-tetramethyl-2,4,5,6-tetrahydrocyclopenta[c]pyrrole with potassium cyanide and potassium acetate in glacial acetic acid using the procedure described above in Example 10 affords 1,2,3,4-tetramethyl-2,4,5,6-tetrahydrocyclopenta[c]pyrrole-4-carbonitrile.

EXAMPLE 10B

A solution of 1.5 g. (0.067 mole) of 4-oxo-1,3-dimethyl-2-phenyl-2,4,5,6-tetrahydrocyclopenta[c]pyrrole, described above in Example 10, and 254 mg. (0.0067 mole) of sodium borohydride in 15 ml. of ethanol was stirred for sixteen hours at 0°–5° C., then for an additional eight hours at ambient temperature and poured into ice/water. The mixture was extracted with ether, and the ether extracts were dried and evaporated to dryness to give 4-hydroxy-1,3-dimethyl-2-phenyl-2,4,5,6-tetrahydrocyclopenta[c]pyrrole as an oil.

The latter, on reaction with potassium cyanide and potassium acetate in glacial acetic acid affords 1,3-dimethyl-2-phenyl-2,4,5,6-tetrahydrocyclopenta[c]pyrrole-4-carbonitrile.

EXAMPLE 11

A mixture of 25.3 g. (0.078 mole) of 2-(4-acetylaminophenyl)-2,4,5,6-tetrahydro-1,3,4,6,6-pentamethylcyclopenta[c]pyrrole-4-carbonitrile, described above in Example 4S, and 7.5 g. (0.12 mole) of 86% aqueous potassium hydroxide in 20 ml. of water and 400 ml. of ethylene glycol was heated under reflux with stirring overnight and the mixture then poured into an ice/water mixture. The solid which separated was collected and recrystallized from isopropanol to give 7 g. of 2-(4-aminophenyl)-2,4,5,6-tetrahydro-1,3,4,6,6-pentamethylcyclopenta[c]pyrrole-4-carbonitrile, m.p. 175°–183° C.

EXAMPLE 12

A mixture of 20 g. (0.066 mole) of 2-phenyl-2,4,5,6-tetrahydro-1,3-diformyl-4,6,6-trimethylcyclopenta[c]pyrrole-4-carbonitrile (described above in Example 9), 200 ml. of diethylene glycol monoethyl ether and 2.5 g. of 10% palladium-on-charcoal was refluxed under nitrogen with stirring for twenty-four hours, then cooled, diluted with methanol to 400 ml. and filtered. The filtrate was taken to dryness, and the residue diluted with water and extracted with ethyl acetate. The ethyl acetate layer was separated, washed four times with water, once with brine, dried, and taken to dryness to give 20.5 g. of a slightly gummy material, which was recrystallized from isopropanol to give 6.5 g. of 2-phenyl-2,4,5,6-tetrahydro-4,6,6-trimethylcyclopenta[c]pyrrole-4-carbonitrile, m.p. 139°–141° C.

EXAMPLE 13

A solution of 11.1 g. (0.04 mole) of 2-phenyl-2,4,5,6-tetrahydro-1,3,4,6,6-pentamethylcyclopenta[c]pyrrole-4-carbonitrile (described in Example 4C) in 160 ml. of absolute ether was cooled to −10° C. and treated dropwise with vigorous stirring with 28.6 g. (0.27 mole) of sulfuryl chloride. The mixture was allowed to stand at room temperature for an additional thirty-two hours, and the solid which separated was then collected to give 7.5 g. of 2-phenyl-1-dichloromethyl-3-trichloromethyl-2,4,5,6-tetrahydro-4,6,6-trimethylcyclopenta[c]pyrrole-4-carbonitrile, m.p. 181°–184° C.

The 4-carbonitrile thus obtained (7.5 g., 0.017 mole) dissolved in 50 ml. of trifluoroacetic acid was treated with a solution of 13.9 g. (0.08 mole) of silver acetate in 120 ml. of trifluoroacetic acid. The mixture was stirred at room temperature for twenty minutes, refluxed under nitrogen for fifteen minutes, and the mixture filtered to remove the solid precipitate. The filtrate was taken to dryness in vacuo, the residue dissolved in ethyl acetate, and the solution was washed first with water, then with brine, dried, and taken to dryness to give 9.2 g. of a pale brown gum which was crystallized from isopropanol to give 5.4 g. of 2-phenyl-1-formyl-3-carboxy-2,4,5,6-tetrahydro-4,6,6-trimethylcyclopenta[c]-pyrrole-4-carbonitrile, m.p. 209°–211° C.

The latter (2.24 g., 0.006 mole) was heated in an oil bath under nitrogen at 240° C. for about sixteen hours, and the residue was recrystallized from methanol to give 533 mg. of 2-phenyl-1-formyl-2,4,5,6-tetrahydro-4,6,6-trimethylcyclopenta[c]pyrrole-4-carbonitrile, m.p. 124°–126° C.

EXAMPLE 13A

Following a procedure similar to that described in Example 13, 125 g. (0.42 mole) of 2-(4-fluorophenyl)-2,4,5,6-tetrahydro-1,3,4,6,6-pentamethylcyclopenta[c]pyrrole-4-carbonitrile, described in Example 4P was reacted with 314 g. (2.32 moles) of sulfuryl chloride to give 74.6 g. of 2-(4-fluorophenyl)-1-dichloromethyl-3-trichloromethyl-2,4,5,6-tetrahydro-4,6,6-trimethylcyclopenta[c]pyrrole-4-carbonitrile.

The latter (50.2 g., 0.107 mole) was reacted with 89.5 g. (0.535 mole) of silver acetate in 1600 ml. of trifluoroacetic acid to give 28.8 g. of 2-(4-fluorophenyl)-1-formyl-3-carboxy-2,4,5,6-tetrahydro-4,6,6-trimethylcyclopenta[c]pyrrole-4-carbonitrile.

The latter (15 g., 0.04 mole) was heated in an oil bath at 115°–120° C. under a nitrogen atmosphere for one hour and the product recrystallized from ethyl acetate to give 5.8 g. of 2-(4-fluorophenyl)-1-formyl-2,4,5,6-tetrahydro-4,6,6-trimethylcyclopenta[c]pyrrole-4-carbonitrile m.p. 165°–168° C.

EXAMPLE 13B

Following a procedure similar to that described in Example 13, 49.6 g. (0.17 mole) of 2-benzyl-2,4,5,6-tetrahydro-1,3,4,6,6-pentamethylcyclopenta[c]pyrrole-4-carbonitrile, described in Example 7A, was reacted with 91.8 g. (0.68 mole) of sulfuryl chloride in 500 ml. of ether to give 33.3 g. of 2-benzyl-1,3-bis-dichloromethyl-2,4,5,6-tetrahydro-4,6,6-trimethylcyclopenta[c]pyrrole-4-carbonitrile, m.p. 139°–141° C.

The latter (47.4 g., 0.11 mole) was hydrolyzed by refluxing in 500 ml. of 50% aqueous ethanol for one hour and the product recrystallized once from ethanol and once from ethyl acetate/hexane to give 4.9 g. of 2-benzyl-1,3-diformyl-2,4,5,6-tetrahydro-4,6,6-trimethylcyclopenta[c]pyrrole-4-carbonitrile, m.p. 107°–109° C.

EXAMPLE 13C

Another procedure for introducing a carboxylic acid group at the 1- or 3-positions of the compounds of Formula II is illustrated by the following:

To a solution of 16.65 g. (0.06 mole) of 2-phenyl-1-formyl-2,4,5,6-tetrahydro-4,6,6-trimethylcyclopenta[c]pyrrole-4-carbonitrile (described in Example 13) in 120 ml. of pyridine and 90 ml. of water at steam bath temperature was added, over a period of 50 minutes, 18.9 g. (0.12 mole) of potassium permanganate. The mixture was then refluxed for an hour, cooled, poured into an aqueous suspension of sodium metabisulfite, acidified to pH 3 with hydrochloric acid, filtered and the solid filter dissolved in benzene. The benzene solution was washed with water, dried, evaporated to dryness and the residue recrystallized from acetonitrile to give 6.2 g. of 2-phenyl-1-carboxy-2,4,5,6-tetrahydro-4,6,6-trimethylcyclopenta[c]pyrrole-4-carbonitrile.

The latter was converted to the methyl ester by addition of 7.25 g. (0.025 mole) of the acid to a stirred suspension of 1.33 g. (0.028 mole) of a 50% mineral oil dispersion of sodium hydride in 50 ml. of dimethylformamide followed by addition of 1.72 ml. (0.028 mole) of methyl iodide. After stirring the reaction mixture for twelve hours, the mixture was poured into ice water, and the solid which separated was collected, dissolved in methylene dichloride, and the solution washed with aqueous sodium bicarbonate, dried and evaporated to dryness to give 7.25 g. of 2-phenyl-1-carbomethoxy-2,4,5,6-tetrahydro-4,6,6-trimethylcyclopenta[c]pyrrole-4-carbonitrile.

EXAMPLE 13D

Following a procedure similar to that described in Example 13C, 17.48 g. (0.06 mole) of 2-phenyl-3-formyl-2,4,5,6-tetrahydro-1,4,6,6-tetramethylcyclopenta[c]pyrrole-4-carbonitrile was oxidized with 18.9 g. (0.12 mole) of potassium permanganate in 120 ml. of pyridine and 90 ml. of water to give 4.03 g. of 2-phenyl-3-carboxy-2,4,5,6-tetrahydro-1,4,6,6-tetramethylcyclopenta[c]pyrrole-4-carbonitrile which was esterified by reaction of 9.83 g. (0.032 mole) of the acid with 1.713 g. (0.035 mole) of a 50% mineral oil dispersion of sodium hydride followed by 2.23 ml. (0.036 mole) of methyl iodide. There was thus obtained 4.18 g. of 2-phenyl-3-carbomethoxy-2,4,5,6-tetrahydro-1,4,6,6-tetramethylcyclopenta[c]pyrrole-4-carbonitrile.

EXAMPLE 14

A mixture of 7.9 g. (0.04 mole) of 1,1,2,2-tetraacetylethane, 3.7 g. (0.04 mole) of aniline and 3.3 g. (0.04 mole) of sodium acetate in 50 ml. of glacial acetic acid was refluxed for one hour and then evaporated to dryness in vacuo. The residue was poured into water, the mixture extracted with chloroform, and the chloroform extracts, after drying, were taken to dryness. The residue was slurried with pentane to give a dark brown crystalline material which was dissolved in benzene and chromatographed on activated magnesium silicate. The major product from the eluate gave yellow crystals on evaporation, which were slurried in pentane to give 4.1 g. of 1-phenyl-2,5-dimethyl-3,4-diacetylpyrrole, m.p. 100°-103° C.

A solution of 10.2 g. (0.04 mole) of 1-phenyl-2,5-dimethyl-3,4-diacetylpyrrole in 100 ml. of tetrahydrofuran was added dropwise with stirring at 0° C. to a solution of 0.15 mole of methyl magnesium bromide in 50 ml. of anhydrous diethyl ether. The mixture was then refluxed for a half hour, cooled, diluted with water and extracted with ether. The combined organic extracts, on drying and evaporation to dryness, afforded an oil which solidified on trituration with hexane. The solid was collected and extracted several times with hot hexane to give 2.5 g. of crude hexane soluble material and 1.9 g. of hexane insoluble material. The hexane soluble and the hexane insoluble crops were each recrystallized from dilute ethanol to give, respectively, 1.7 g. and 1.9 g. samples of 1-phenyl-2,5-dimethyl-3,4-di-(2-hydroxy-2-propyl)pyrrole, m.p. 113°-116° C. and 112°-114° C, respectively.

A solution of 1.6 g. (0.006 mole) of 1-phenyl-2,5-dimethyl-3,4-di-(2-hydroxy-2-propyl)pyrrole and 0.8 g. (0.012 mole) of potassium cyanide in 30 ml. of glacial acetic acid was refluxed for four hours, then poured into water and the mixture extracted with ether. The ether extracts, on washing with water, drying over sodium sulfate, and evaporation to dryness, gave an oil which was identified through its n.m.r. and mass spectra as 2-phenyl-2,4,5,6-tetrahydro-1,3,4,6,6-pentamethylcyclopenta[c]pyrrole-4-carbonitrile described above in Example 4C.

EXAMPLE 15

A mixture of 59.4 g. (0.3 mole) of 1,1,2,2-tetraacetylethane, 27.9 g. (0.3 mole) of aniline and 40 g. of sodium acetate in 400 ml. of glacial acetic acid was heated under reflux for three hours, then cooled and concentrated to a small volume in vacuo. The residue was treated with water, and the solid which separated was collected, washed with water, dried and recrystallized from cyclohexane to give two crops totaling 64 g. of 1-phenyl-2,5-dimethyl-3,4-di-acetylpyrrole, m.p. 96°-99° C.

The latter (10.2 g., 0.04 mole) in 100 ml. of tetrahydrofuran was treated at 0° C. with 50 ml. (0.15 mole) of a 3M solution of methyl magnesium bromide in diethyl ether. The solution was heated under reflux for one-half hour, then cooled, treated with water, and the organic layer separated and washed with brine. Evaporation of the organic extracts to dryness afforded a solid material which was recrystallized from aqueous ethanol to give two crops (1.7 g. and 1.9 g.) of 3,5-dihydro-1,1,3,3,4,6-hexamethyl-5-phenyl-1H-furo[3,4-c]-pyrrole, m.p. 113°-116° C. and 112°-114° C., respectively.

A solution of 1.6 g. (0.0059 mole) of the latter and 0.8 g. (0.012 mole) of potassium cyanide in 30 ml. of glacial acetic acid was stirred at room temperature for about forty-eight hours and then at reflux temperature for about seven hours. The mixture was poured into water and the mixture extracted with diethyl ether. The organic extracts were washed with water, dried over sodium sulfate, and evaporated to dryness to give a brown oil whose mass spectrum and nuclear magnetic resonance spectrum showed the product to be largely 2-phenyl-2,4,5,6-tetrahydro-1,3,4,6,6-pentamethylcyclopenta[c]pyrrole-4-carbonitrile, described above in Example 4C.

EXAMPLE 16

To a solution of 6 g. (0.03 mole) of 1-phenyl-2,5-dimethyl-3-acetylpyrrole in 60 ml. of tetrahydrofuran was added 15 ml. of a 0.045 molar solution of methyl magnesium bromide in ether and the solution maintained at 0°-5° C. for twenty-four hours. The mixture was then poured into a saturated solution of ammonium chloride and extracted with ether. The ether extracts, on drying and evaporation to dryness afforded 7 g. of 1-phenyl-2,5-dimethyl-3-(1-methyl-1-hydroxy)ethylpyrrole.

A solution of 2.3 g. (0.01 mole) of the latter, 1.3 g. (0.02 mole) of potassium cyanide, 1.99 g. (0.02 mole) of potassium acetate and 0.73 ml. (0.01 mole) of acetone in 20 ml. of glacial acetic acid was refluxed for six hours on a steam bath and then stirred at ambient temperature for twelve hours. The mixture in a water immiscible solvent was extracted first with dilute ammonium hydroxide to remove all acetic acid and then with saturated ammonium chloride. Evaporation of the solvent gave material which was shown by nmr to consist of 40% 1-phenyl-2,5-dimethylpyrrole and 60% 2-phenyl-2,4,5,6-tetrahydro-1,3,4,6,6-pentamethylcyclopenta[c]pyrrole-4-carbonitrile.

EXAMPLE 17

A solution of 5.84 g. (0.02 mole) of 2-phenyl-3-formyl-1,4,6,6-tetramethyl-2,4,5,6-tetrahydrocyclopenta[c]pyrrole-4-carbonitrile, described in Example 9A, in 200 ml. of tetrahydrofuran was cooled to −5° C.

under nitrogen and then treated with 11.4 ml. of a 2.1 molar solution of diethyl aluminum cyanide in benzene, the solution stirred for two and a half hours and then poured into 300 g. of ice and 10 ml. of acetic acid. Extraction of the mixture with benzene and concentration of the extracts to dryness after washing and drying gave 5.4 g. of crude product which was triturated several times with benzene and once with hexane to give 4.2 g. of 2-phenyl-1,4,6,6-tetramethyl-3-(hydroxycyanomethyl)-2,4,5,6-tetrahydrocyclopenta[c]-pyrrole-4-carbonitrile, m.p. 133°–134° C.

EXAMPLE 18

Reduction of the 2-(4-fluorophenyl)-1-formyl-3-carboxy-2,4,5,6-tetrahydro-4,6,6-trimethylcyclopenta[c-]pyrrole-4-carbonitrile and 2-benzyl-1,3-diformyl-2,4,5,6-tetrahydro-4,6,6-trimethylcyclopenta[c]pyrrole-4-carbonitrile described in Examples 13A and 13B, respectively, with sodium borohydride using the procedure described in Example 10B, gave the following compounds of Formula II where $R_3$, $R_4$ and $R_5$ are $CH_3$.

Table 18

| Example | $R_6(1)$ | $R_6(3)$ | $R_7$ | Wt. S.M. | Wt. Prod. | m.p.(° C.)/Solvent |
|---|---|---|---|---|---|---|
| 18A | $CH_2OH$ | COOH | $4-FC_6H_4$ | 3.4 | 1.0 | 188/methanol-water |
| 18B | $CH_2OH$ | $CH_2OH$ | $C_6H_5CH_2$ | 10.0 | 3.6 | 172.5–174.5/ethanol-benzene |

EXAMPLE 19

A solution of 6.12 g. (0.02 mole) of 2-phenyl-2,4,5,6-tetrahydro-1,3-diformyl-4,6,6-trimethylcyclopenta[c-]pyrrole-4-carbonitrile, described above in Example 9, 2.08 g. (0.02 mole) of 2,2-dimethyl-1,3-propanediol and 0.1 g. of p-toluene-sulfonic acid hydrate was refluxed under a water separator for about twelve hours and then washed with dilute sodium bicarbonate. The extracts, on drying and evaporation to dryness, gave 8 g. of crude material which was recrystallized from cyclohexane to give 5.7 g. of 2-phenyl-1-formyl-4,6,6-trimethyl-3-(5,5-dimethyl-1,3-dioxan-2-yl)-2,4,5,6-tetrahydrocyclopenta[c]pyrrole-4-carbonitrile, m.p. 175°–177° C.

EXAMPLE 19A

Similarly prepared from 9.19 g. (0.03 mole) of 2-phenyl-2,4,5,6-tetrahydro-1,3-diformyl-4,6,6-trimethylcyclopenta[c]pyrrole-4-carbonitrile, 3.85 ml. of 2-methylpentane-2,4-diol and 0.1 g. of p-toluenesulfonic acid in 80 ml. of benzene was 2-phenyl-1-formyl-4,6,6-trimethyl-3-(4,4,6-trimethyl-1,3-dioxan-2-yl)cyclopenta[c]pyrrole-4-carbonitrile, m.p. 143°–144° C. (6.35 g., from cyclohexane).

II. FINAL PRODUCTS

EXAMPLE 20

A mixture of 22 g. (0.10 mole) of 2,4,5,6-tetrahydro-1,2,3,4,6,6-hexamethylcyclopenta[c]pyrrole-4-carbonitrile in 10 ml. of water and 100 ml. of concentrated sulfuric acid was warmed to 85° C., on a steam bath and heated with stirring for about five minutes. The resulting dark brown solution was poured into water, basified with 35% aqueous sodium hydroxide until no further solid separated, and the solid which precipitated was collected, washed with water, air dried, and recrystallized with charcoaling from ethyl acetate to give 17.3 g. of 2,4,5,6-tetrahydro-1,2,3,4,6,6-hexamethylcyclopenta[c]pyrrole-4-carboxamide, m.p. 184.5°–187.5° C.

Following a procedure similar to that described in Example 1, using an appropriate 2,4,5,6-tetrahydro-4,6,6-trimethylcyclopenta[c]pyrrole-4-carbonitrile of Formula II, the following 2,4,5,6-tetrahydro-4,6,6-trimethylcyclopenta[c]pyrrole-4-carboxamides of Formula I were prepared, where in each instance, $R_1$ and $R_2$ are each hydrogen; X is 0; and $R_3$, $R_4$ and $R_5$ are each $CH_3$.

Table 20a

| Example | $R_6$ | $R_7$ | Wt. II | Wt. I | m.p. (° C.)/Solvent |
|---|---|---|---|---|---|
| 20A | $CH_3$ | H | 60 | 28 | 230–233/ethyl acetate |
| 20B | $CH_3$ | $CH_2CH_2CH_2N(CH_3)_2$ | 29.3 | 19 | 114.5–116/acetonitrile |
| 20C | $CH_3$ | $-(CH_2)_6-$ | 45 | 10.5 | 218–221/DMF |
| 20D | $CH_3$ | $CH_2CH_2C_6H_5$ | 56 | 17.8 | 115.5–117.5/cyclohexane |
| 20E | $CH_3$ | $4-NH_2SO_2C_6H_4$ | 44 | 1.8 | 258–260/methanol |
| 20F | $CH_3$ | $C_6H_5$ | 28 | 18 | 140/cyclohexane |
| 20G | $CH_3$ | $C_2H_5$ | 37.2 | 15.2 | 162–164/ethyl acetate |
| 20H | $CH_3$ | $C_3H_7$ | 40 | 34.4 | 164.5–166.5/isopropanol |
| 20J | $CH_3$ | $CH_2C_6H_5$ | 24 | 20.2 | 170–171/ethyl acetate |
| 20K | $CH_3$ | $4-CH_3OC_6H_4$ | 70 | 37 | 198.5–201/isopropanol |
| 20L | $CH_3$ | $4-CH_3C_6H_4$ | 58.4 | 32 | 198–202/acetonitrile |
| 20M | $CH_3$ | $4-ClC_6H_4$ | 62.5 | 34 | 165.5–167.5/acetonitrile |
| 20N | $CH_3$ | $3-ClC_6H_4$ | 81.4 | 60 | 139–142/acetonitrile |
| 20P | $CH_3$ | 2-pyridyl | 86 | 32 | 187–189/acetonitrile |
| 20Q | $CH_3$ | $3-CH_3C_6H_4$ | 60 | 27.4 | 149.5–151.5/methanol |
| 20R | $CH_3$ | $2-ClC_6H_4$ | 116 | 14.7 | 181–183/methanol |
| 20S | $CH_3$ | $2-CH_3C_6H_4$ | 100 | 28 | 159–161/methanol |
| 20T | $CH_3$ | $4-FC_6H_4$ | 88 | 54 | 150–151/isopropanol |
| 20U | $CH_3$ | $4-(CH_3)_2NC_6H_4$ | 64.2 | 31.5 | 238–241/DMF |
| 20V | $CH_3$ | $4-HOC_6H_4$ | 88.2 | 31.7 | 249–251/methanol |
| 20W | $CH_3$ | $4-CH_3CONHC_6H_4$ | 55 | 22 | 236–239/methanol |
| 20X | $CH_3$ | $CH_2CH_2CONH_2$ | 23.9 | 4.3 | 130.5–133/acetone |
| 20Y | $CH_3$ | $C_4H_9$ | 30.7 | 7.8 | 135–137/cyclohexane |
| 20Z | $CH_3$ | iso-$C_3H_7$ | 25.6 | 13.5 | 156–158/cyclohexane |
| 20AA | $CH_3$ | $CH_2CH_2OC_2H_5$ | 103.1 | 21.5 | 109–111/hexane |
| 20AB | CHO | $C_6H_5$ | 10 | 3.4 | 164.5–166.5/methanol |
| 20AC | $CH_3$ | $CH_2COOC_2H_5$ | 55 | 33.5 | 138–140/ether-ethanol |
| 20AD | $CH_3$ | cyclohexyl | 81 | 31 | 125–150/isopropanol |
| 20AE | $CH_3$ | cyclopropyl | 12.1 | 10.1 | 188–192 |
| 20AF | $CH_3$ | cyclopentyl | 6.9 | 4.6 | 152–155/cyclohexane |
| 20AG | $CH_3$ | $CH_2CH_2N(CH_3)_2$ | 1.9 | 0.5 | 110–113/heptane-hexane |

Table 20a-continued

| Example | R₆ | R₇ | Wt. II | Wt. I | m.p. (° C.)/Solvent |
|---|---|---|---|---|---|
| 20AH | CH₃ | CH₂CH₂N(CH₂CH₂)₂O | 9.8 | 8.6 | 142–144/hexane |
| 20AJ | CH₃ | CH₂CH₂CH₂OH | 2.6 | | |
| 20AK | CH₃ | cyclobutyl | 9.3 | 5.5 | 149–152 |
| 20AL | CH₃ | cyclopropyl-CH₂ | 25 | 10.9 | 150–153/ethanol-H₂O |
| 20AM | H | C₆H₅ | 0.500 | 0.500 | 192–194/methanol |
| 20AN | CH₃ | sec-C₄H₉ | 40 | 29.3 | 152–154/cyclohexane |
| 20AP | CH₃ | iso-C₄H₉ | 18.5 | 12.0 | 148.5–151/hexane |
| 20AQ | CH₃ | 3,4-(HO)₂C₆H₃ | 5.0* | 2.3 | 129–131/ethyl acetate-pentane |
| 20AR | CH₃ | 4-C₂H₅OC₆H₄ | 45 | 8 | 212–214/ethanol-H₂O |
| 20AS | CH₃ | 3-CF₃C₆H₄ | 6.3 | 4.0 | 150–153/benzene-pentane |
| 20AT | CH₃ | CH₂C≡CH | 22.6 | 14.7 | 141–145/cyclohexane |
| 20AU | CH₃ | 3,4-(CH₃O)₂C₆H₃ | 23.3 | 8.1 | 182–184/acetonitrile |
| 20AV | CH₃ | CH₂CH₂F | 17.7 | 11.1 | 130–131/benzene-hexane |
| 20AW | CH₃ | CH₂CH₂Cl | 20.0 | 17.3 | 145.5–147/benzene-hexane |
| 20AX | C₂H₅ | C₆H₅ | 10.3 | 9.0 | 152–153 |
| 20AY | +CHO(1) H(3) | C₆H₅ | 6.3 | 4.2 | 190–192/isopropanol |
| 20AZ | CHO(1) CH₃(3) | C₆H₅ | 29.8 | 1.0 | 123–126/benzene |
| 20BA | CHO(1) COOH(3) | 4-FC₆H₄ | 6.1 | 1.0 | 241 (dec.)/methanol |
| 20BB | CHO(1) COOH(3) | C₆H₅ | 14.0 | 7.9 | 231–232/acetone |
| 20BC | CHO(1) H(3) | 4-FC₆H₄ | 5.0 | 3.7 | 193–196/isopropanol |
| 20BD | CH₃(1) COOCH₃(3) | C₆H₅ | 3.0 | 3.1 | -/ether-hexane |
| 20BE | COOCH₃(1) H(3) | C₆H₅ | 6.0 | 5.09 | -/ether-hexane |

*Starting material was 1-[3,4-(2,2-propylenedioxy)phenyl] compound described in Example 4AG.
+Product is 1-formyl compound prepared from compound of Example 13.

Following a procedure similar to that described in Example 20, using an appropriate 2,4,5,6-tetrahydrocyclopenta[c]pyrrole-4-carbonitrile of Formula II in refluxing 90% aqueous sulfuric acid, the following compounds of Formula I, where, in each instance, R₁ and R₂ are each hydrogen; and X is 0, are prepared.

Table 20b

| Example | R₃ | R₄ | R₅ | R₆ | R₇ |
|---|---|---|---|---|---|
| 20BF | CH₃ | CH₃ | CH₃ | CH₃ | 4-BrC₆H₄ |
| 20BG | CH₃ | CH₃ | CH₃ | CH₃ | 2,4,6-Cl₃C₆H₂ |
| 20BH | CH₃ | CH₃ | CH₃ | CH₃ | 2-Cl-4-CH₃C₆H₃ |
| 20BJ | CH₃ | CH₃ | CH₃ | CH₃ | 3,4—OCH₂OC₆H₃ |
| 20BK | CH₃ | CH₃ | CH₃ | CH₃ | 4-CF₃C₆H₄ |
| 20BL | CH₃ | CH₃ | CH₃ | CH₃ | 2,4,6-(CH₃)₃C₆H₂ |
| 20BM | CH₃ | CH₃ | CH₃ | CH₃ | CH₂CH₂SC₂H₅ |
| 20BN | CH₃ | CH₃ | CH₃ | C₃H₇ | C₆H₅ |
| 20BP | CH₃ | CH₃ | CH₃ | iso-C₃H₇ | C₆H₅ |
| 20BQ | CH₃ | CH₃ | CH₃ | C₄H₉ | C₆H₅ |
| 20BR | CH₃ | H | H | CH₃ | C₆H₅ |
| 20BS | CH₃ | H | H | CH₃ | CH₃ |
| 20BT | CH₃ | CH₃ | CH₃ | CH₃ | 4-NH₂C₆H₄ |
| 20BU | CH₃ | CH₃ | CH₃ | CH₃ | cyclohexyl-CH₂ |
| 20BV | CH₃ | CH₃ | CH₃ | CH₃ | CH₂CH₂N(CH₂)₄ |
| 20BW | CH₃ | CH₃ | CH₃ | CH₃ | CH₂CH₂N(CH₂)₅ |
| 20BX | H | H | H | CH₃ | CH₃ |
| 20BY | CH₃ | CH₃ | CH₃ | CH₃ | 2-thienyl |
| 20BZ | CH₃ | CH₃ | CH₃ | CH₃ | 4-HOOCC₆H₄ |
| 20CA | CH₃ | CH₃ | CH₃ | CH₃ | 3-H₂NCOC₆H₄ |
| 20CB | CH₃ | CH₃ | CH₃ | CH₃ | 3-CH₃SC₆H₄ |
| 20CC | CH₃ | CH₃ | CH₃ | CH₃ | 4-O₂NC₆H₄ |
| 20CD | CH₃ | CH₃ | CH₃ | C₆H₅CH₂ | C₆H₅ |
| 20CE | CH₃ | CH₃ | CH₃ | CH₃ | 3-pyridyl |
| 20CF | CH₃ | CH₃ | CH₃ | CH₃ | 9-acridinyl |
| 20CG | CH₃ | CH₃ | CH₃ | CH₃ | 4-(2,1,3-benzothiazolyl) |
| 20CH | CH₃ | CH₃ | CH₃ | CH₃ | 2-benzothiazolyl |
| 20CJ | CH₃ | CH₃ | CH₃ | CH₃ | 3-carbazolyl |
| 20CK | CH₃ | CH₃ | CH₃ | CH₃ | 2-benzoxazolyl |
| 20CL | CH₃ | CH₃ | CH₃ | CH₃ | 2-purinyl |
| 20CM | CH₃ | CH₃ | CH₃ | CH₃ | 6-purinyl |
| 20CN | CH₃ | CH₃ | CH₃ | CH₃ | 2-pyrazinyl |
| 20CP | CH₃ | CH₃ | CH₃ | CH₃ | 4-pyrimidinyl |
| 20CQ | CH₃ | CH₃ | CH₃ | CH₃ | 20-thiazolyl |
| 20CR | CH₃ | CH₃ | CH₃ | CH₃ | 3-pyrazolyl |
| 20CS | CH₃ | CH₃ | CH₃ | CH₃ | 2-pyrimidinyl |
| 20CT | CH₃ | CH₃ | CH₃ | CH₃ | 6-pyrimidinyl |

Table 20b-continued

| Example | R₃ | R₄ | R₅ | R₆ | R₇ |
|---|---|---|---|---|---|
| 20CU | CH₃ | CH₃ | CH₃ | CH₃ | 2-benzimidazolyl |
| 20CV | CH₃ | CH₃ | CH₃ | CH₃ | 2-benzothiazolyl |
| 20CW | CH₃ | CH₃ | CH₃ | CH₃ | 5-indazolyl |
| 20CX | CH₃ | CH₃ | CH₃ | CH₃ | 6-indazolyl |
| 20CY | CH₃ | CH₃ | CH₃ | CH₃ | 7-indazolyl |
| 20CZ | CH₃ | CH₃ | CH₃ | CH₃ | 5-isoquinolinyl |
| 20DA | CH₃ | CH₃ | CH₃ | CH₃ | 3-pyridazinyl |
| 20DB | CH₃ | CH₃ | CH₃ | CH₃ | 2-thiadiazolyl |
| 20DC | CH₃ | CH₃ | CH₃ | CH₃ | 5-tetrazolyl |
| 20DD | CH₃ | CH₃ | CH₃ | CH₃ | 2-thiazolinyl |
| 20DE | CH₃ | CH₃ | CH₃ | CH₃ | 3-(1,2,4-triazinyl) |
| 20DF | CH₃ | CH₃ | CH₃ | CH₃ | 3-(1,2,4-triazolyl) |

EXAMPLE 21

A mixture of 25 g. (0.09 mole) of 2-phenyl-2,4,5,6-tetrahydro-1,3,4,6,6-pentamethylcyclopenta[c]pyrrole-4-carbonitrile described above in Example 4C, 100 ml. of absolute ethanol and 25 ml. of 35% aqueous sodium hydroxide was refluxed on a steam bath for seventy hours, and the mixture then diluted with 250 ml. of water. The oil which separated crystallized on cooling and was collected, washed, and dried to give 17 g. of 2-phenyl-2,4,5,6-tetrahydro-1,3,4,6,6-pentamethylcyclopenta[c]pyrrole-4-carboxamide, m.p. 123°–130° C. identical with the compound described above in Example 20F.

EXAMPLE 22

To a stirred mixture of 10.5 g. (0.24 mole) of a 57% dispersion of sodium hydride in mineral oil (which was washed and decanted with hexane to remove the mineral oil) in 100 ml. of dimethylsulfoxide was added a solution of 29.6 g. (0.1 mole) of 2-phenyl-2,4,5,6-tetrahydro-1,3,4,6,6-pentamethylcyclopenta[c]pyrrole-4-carboxamide dissolved in 200 ml. of dimethylsulfoxide. The reaction mixture was stirred for about one and a half hours until evolution of hydrogen ceased, and then treated dropwise with 35.5 g. (0.25 mole) of methyl iodide. After stirring for an additional two hours, the mixture was diluted with about 10 ml. of water, poured onto ice, and the white precipitate was removed by filtration. The filtrate was extracted with ether, added to an ether solution of the solid, and the combined organic solution washed several times with water, dried over sodium sulfate, and evaporated to dryness.

The resulting yellow oil (35.3 g.) was dissolved once again in 200 ml. of dimethylsulfoxide, added to a suspension of 6.0 g. of sodium hydride in dimethylsulfoxide, the mixture warmed to 75° C. for about five minutes, treated with 18 g. of methyl iodide as above, and then stirred for one hour at room temperature. The reaction mixture, when worked up in the manner described above, afforded 31.3 g. of a yellow oil which slowly crystallized and which was recrystallized from a methanol/water mixture to give 27.7 g. of 2-phenyl-2,4,5,6-tetrahydro-1,3,4,6,6-pentamethylcyclopenta[c]pyrrole-4-N,N-dimethylcarboxamide, m.p. 100°–104° C.

Following a procedure similar to that described in Example 22, using an appropriate 2,4,5,6-tetrahydro-1,3,4,6,6-pentamethylcyclopenta[c]pyrrole-4-carboxamide and an appropriate lower-alkyl halide, the following compounds of Formula I, where in each instance $R_3$, $R_4$, $R_5$ and both $R_6$ groups are each $CH_3$, and X is 0, are prepared.

Table 22

| Example | $R_1$ | $R_2$ | $R_7$ |
|---------|-------|-------|-------|
| 22A | $CH_3$ | H | $CH_3$ |
| 22B | $CH_3$ | $CH_3$ | $CH_3$ |
| 22C | $CH_3$ | H | $CH_2CH_2CH_2N(CH_3)_2$ |
| 22D | $CH_3$ | $CH_3$ | $CH_2CH_2CH_2N(CH_3)_2$ |
| 22E | $CH_3$ | H | $CH_2CH_2C_6H_5$ |
| 22F | $CH_3$ | $CH_3$ | $CH_2CH_2C_6H_5$ |
| 22G | $CH_3$ | H | $C_6H_5$ |
| 22H | $CH_3$ | H | 2-pyridyl |
| 22J | $CH_3$ | $CH_3$ | 2-pyridyl |

EXAMPLE 23

A 2.53 g. (0.06 mole) portion of a 57% dispersion of sodium hydride in mineral oil was washed free of mineral oil by slurrying and decantation with hexane, and was then slurried in 40 ml. of dimethylsulfoxide. To the mixture was added a solution of 8.8 g. (0.04 mole) of 2,4,5,6-tetrahydro-1,3,4,6,6-pentamethylcyclopenta[c]pyrrole-4-carboxamide (described above in Example 20A), and the mixture was stirred at room temperature for one hour. The mixture was then treated with 8.1 g. (0.06 mole) of cyclopropylmethyl bromide, stirred at room temperature overnight, poured into water, and the mixture extracted with diethyl ether. The ether extracts, on drying and evaporation to dryness, afforded a brown oil which was chromatographed on silica gel using a 3% isopropanol in ether solution as eluent. There was thus obtained a crystalline material which was slurried with ether/pentane to give 0.55 g. of 2-cyclopropylmethyl-2,4,5,6-tetrahydro-1,3,4,6,6-pentamethylcyclopenta[c]pyrrole-4-carboxamide, m.p. 145°–148° C. identical with that described above in Example 20AL.

EXAMPLE 24

To a solution of 4.45 g. (0.013 mole) of 2-phenyl-1-hydroxymethyl-3-carboxy-2,4,5,6-tetrahydro-4,6,6-trimethylcyclopenta[c]pyrrole-4-carboxamide in 15 ml. of dimethylformamide was added 0.61 g. (0.014 mole) of a 57% mineral oil dispersion of sodium hydride, the mixture was stirred for two hours and then treated with 0.8 g. of methyl iodide and stirred at ambient temperature for about twelve hours. The mixture was then poured into water, and the solid was collected and recrystallized from acetone to give 2.3 g. of 2-phenyl-1-hydroxymethyl-3-carbomethoxy-2,4,5,6-tetrahydro-4,6,6-trimethylcyclopenta[c]pyrrole-4-carboxamide, m.p. 226–227° C.

EXAMPLE 25

A solution of 3.05 g. (0.01 mole) of 2-[3-(dimethylamino)propyl]-2,4,5,6-tetrahydro-1,3,4,6,6-pentamethylcyclopenta[c]pyrrole-4-carboxamide (described above in Example 20B) in 30 ml. of isopropanol was treated with 2.1 g. of methyl iodide, and the mixture was allowed to stand at room temperature overnight. The material which had separated was then collected, washed with isopropanol and pentane and dried to give 4.5 g. of 2-[3-(dimethylamino)propyl]-2,4,5,6-tetrahydro-1,3,4,6,6-pentamethylcyclopenta[c]pyrrole-4-carboxamide methiodide, m.p. 128°–130° C.

A solution of 10.2 g. (0.06 mole) of silver nitrate in 102 ml. of hot water was treated with a solution of 2.34 g. of sodium hydroxide in 24 ml. of hot water. The resulting precipitate was washed five times by decantation with hot water, then filtered, and the solid added to a solution of about 9 g. (0.02 mole) of 2-[3-(dimethylamino)propyl]-2,4,5,6-tetrahydro-1,3,4,6,6-pentamethylcyclopenta[c]pyrrole-4-carboxamide methiodide in 60 ml. of water. The mixture was stirred at room temperature overnight, then filtered, the filter washed first with hot water and then with ethanol, the aqueous and the ethanol filtrates being set aside separately for further work. The ethanol washings were refiltered, evaporated to dryness, and the solid residue which slowly crystallized was set aside and combined with organic material obtained by evaporation to dryness of the aqueous filtrate, heating the solid residue on a steam bath for three hours under a vacuum pump, extraction of the residue with ethyl acetate and evaporation to dryness of the extracts. The combined material obtained from the aqueous and ethanol washings was recrystallized from ethyl acetate/pentane to give two crops totaling 0.7 g. of 2-allyl-2,4,5,6-tetrahydro-1,3,4,6,6-pentamethylcyclopenta[c]pyrrole-4-carboxamide, m.p. 96°–98° C.

EXAMPLE 26

To a suspension of 1.025 g. of 2-phenyl-2,4,5,6-tetrahydro-1,3-diformyl-4,6,6-trimethylcyclopenta[c]pyrrole-4-carboxamide (described above in Example 20AB) in 10 ml. of ethanol was added with stirring a suspension of 250 mg. of sodium borohydride in ethanol, and the resulting clear solution was allowed to stand at room temperature for two hours. The white crystalline solid which separated was collected, washed with water and dried to give 645 mg. of product. This material was combined with that obtained by evaporation to dryness of the filtrate from the main product and trituration with water and collection and drying of the residual solid. There was thus obtained an additional 344 mg. of 2-phenyl-2,4,5,6-tetrahydro-1,3-bishydroxymethyl-4,6,6-trimethylcyclopenta[c]pyrrole-4-carboxamide ethanolate, m.p. 115°–120° C.

Following a procedure similar to that described in Example 26, the following compounds of Formula I, where in each instance $R_1$ and $R_2$ are each hydrogen and $R_3$, $R_4$ and $R_5$ are each methyl, were prepared.

Table 26

| Example | $R_6$ | $R_7$ | Wt.S.M. | Wt.Prod. | m.p.(° C.)/Solvent |
|---|---|---|---|---|---|
| 26A | $CH_2OH(1)$ $H(3)$ | $C_6H_5$ | 2.0 | 1.59 | 170–171/ethyl acetate |
| 26B | $CH_2OH(1)$ $CH_3(3)$ | $C_6H_5$ | 2.3 | 1.8 | 184–185 |
| 26C | $CH_2OH(1)$ $COOH(3)$ | $4\text{-}FC_6H_4$ | 3.0 | 2.0 | 140–190/ethyl acetate |
| 26D | $CH_2OH(1)$ $COOH(3)$ | $C_6H_5$ | 6.11 | 3.37 | 150–185/ethyl acetate |
| 26E | $CH_2OH(1)$ $H(3)$ | $4\text{-}FC_6H_4$ | 2.0 | 1.3 | 182–183/benzene |
| 26F | $H(1)$ $CH_2OH(3)$ | $C_6H_5$ | 2.8 | 2.3 | 158–159/benzene |
| 26G | $CH_3(1)$ $CH_2OCH(CH_3)_2(3)$* | $C_6H_5$ | 401 | 4.3* | 144–147/isopropanol |
| 26H | $CH_3(1)$ $CH_2OH(3)$ | $C_6H_5$ | 1.0 | 0.9 | 173–179/aqueous ethanol |
| 26J | $CH_2OH$ | $C_6H_5$ | 6.2 | 1.0 | 116.5–118.5/ethanol |

*Obtained by recrystallizing 10 g. (of 444 g. obtained) of the corresponding 3-hydroxymethyl compound.

EXAMPLE 27

A solution of 10 g. (0.034 mole) of 2-phenyl-2,4,5,6-tetrahydro-1,3,4,6,6-pentamethylcyclopenta[c]pyrrole-4-carboxamide in 4.5 liters of chloroform was stirred under a high intensity light while bubbling air through the mixture for about sixteen hours. The mixture was then taken to dryness in vacuo and the residue dissolved in benzene and chromatographed on a column of activated magnesium silicate, the product being eluted first with benzene and then with ether. The combined eluates were diluted with ethyl acetate, and the solid which separated was collected and dried to give 1.05 g. of material which was shown by its n.m.r. and mass spectra and by chemical analysis to be 2-phenyl-3-formyl-2,4,5,6-tetrahydro-1,4,6,6-tetramethylcyclopenta[c]pyrrole-4-carboxamide, m.p. 201°–204° C.

In another experiment, a solution of 75 mg. of 2-phenyl-2,4,5,6-tetrahydro-1,3,4,6,6-pentamethylcyclopenta[c]pyrrole-4-carboxamide in a concentration of 1 mg./ml. in chloroform was exposed to sunlight for about five days and the solution then evaporated to a concentration of 10 mg./ml., chromatographed on alumina and eluted with 1:1 chloroform/methanol. A total of five bands was developed, the first of which yielded 7.8 mg. and the third 33.3 mg. of material both of whose mass spectra showed a molecular ion of 310 (calculated 308.4) and whose n.m.r. spectrum showed the first to be 2-phenyl-1-formyl-2,4,5,6-tetrahydro-3,4,6,6-tetramethylcyclopenta[c]pyrrole-4-carboxamide, identical with the compound described above in Example 20AZ, and the third to be the isomeric 2-phenyl-3-formyl-2,4,5,6-tetrahydro-1,4,6,6-tetramethylcyclopenta[c]pyrrole-4-carboxamide.

EXAMPLE 28

2-Phenyl-1-formyl-2,4,5,6-tetrahydro-4,6,6-trimethylcyclopenta[c]pyrrole-4-carbonitrile (described in Example 13) (8.35 g., 0.03 mole) was combined with 4.6 ml. of 85% hydrazine hydrate, 5.25 g. of solid potassium hydroxide and 50 ml. of triethylene glycol, and the mixture was refluxed for one and one half hours under nitrogen. The low boiling components were distilled off until the pot temperature reached 205° C., and the mixture was then heated an additional two hours at that temperature. The mixture was cooled, poured into ice water, and extracted with ethyl acetate. The aqueous phase was acidified with concentrated sulfuric acid, and the solid which separated was collected and dried to give 6.2 g. of 2-phenyl-2,4,5,6-tetrahydro-1,4,6,6-tetramethylcyclopenta[c]pyrrole-4-carboxylic acid.

The latter (6.18 g., 0.22 mole) was dissolved in 70 ml. of tetrahydrofuran, the solution treated with 4.25 g. (0.026 mole) of N,N'-carbonyldiimidazole, and the solution stirred for six hours at room temperature. A solution of 5 ml. of liquid ammonia in 20 ml. of tetrahydrofuran was then added gradually and the solution stirred at room temperature for about fifteen hours. The solid which separated was collected and dissolved in ethyl acetate and the solution washed first with dilute alkali, then with brine, dried and taken to dryness. The pale yellow residual solid was recrystallized once from ethyl acetate and once from methanol to give 1 g. of 2-phenyl-2,4,5,6-tetrahydro-1,4,6,6-tetramethylcyclopenta[c]pyrrole-4-carboxamide, m.p. 185°–202° C.

EXAMPLE 29

A solution of 25 g. of 2-phenyl-2,4,5,6-tetrahydro-1,3,4,6,6-pentamethylcyclopenta[c]pyrrole-4-carboxamide (described in Example 20F) in 500 ml. of chloroform containing about 0.75% ethanol was stirred at ambient temperature for four days while bubbling air through the solution. The solution was then taken to dryness and the residue eluted with diethyl ether/hexane. There was thus obtained material having m.p. 95°–100° C. whose mass spectrum showed a molecular ion of 384 (calculated 384) and which was shown from its n.m.r. spectrum to be 2-phenyl-1,3-diethoxymethyl-2,4,5,6-tetrahydro-4,6,6-trimethylcyclopenta[c]pyrrole-4-carboxamide.

The latter on reaction with hydrochloric acid in chloroform afforded a mixture which was separated by chromatography into two components, the major component being 2-phenyl-3-formyl-2,4,5,6-tetrahydro-1,4,6,6-tetramethylcyclopenta[c]pyrrole-4-carboxamide and the minor being the isomeric 2-phenyl-1-formyl-2,4,5,6-tetrahydro-3,4,6,6-tetramethylcyclopenta[c]pyrrole-4-carboxamide which were shown by their mass and n.m.r. spectra to be identical with the respective compounds described above in Example 27.

EXAMPLE 30

A solution of 2.0 g. (0.006 mole) of the 2-phenyl-2,4,5,6-tetrahydro-1,3-bishydroxymethyl-4,6,6-trimethylcyclopenta[c]pyrrole-4-carboxamide described in Example 26J in 50 ml. of methanol was treated with 0.11 g. of p-toluene-sulfonic acid, the solution was stirred at room temperature for an hour and a half and then taken to dryness. The residue was dissolved in methylene dichloride, the solution washed with saturated sodium bicarbonate and brine, then dried over sodium sulfate and taken to dryness, and the crude product recrystallized from benzene/hexane to give 2.2 g. of 2-phenyl-2,4,5,6-tetrahydro-1,3-bismethoxymethyl-4,6,6-trimethylcyclopenta[c]pyrrole-4-carboxamide, m.p. 168°–169.5° C.

EXAMPLE 31

A mixture of 15.0 g. (0.05 mole) of 2-phenyl-2,4,5,6-tetrahydro-1,3,4,6,6-pentamethylcyclopenta[c]pyrrole-4-carboxamide (described in Example 20F), 15.0 g. (0.38 mole) of sodium hydroxide, 150 ml. of ethylene glycol and 1.0 ml. of water was refluxed in a stainless steel round bottom flask for two days. The mixture was then cooled, poured into about one liter of water and acidified with glacial acetic acid. The solid which separated was washed with water and recrystallized from methanol to give 8.0 g. of 2-phenyl-2,4,5,6-tetrahydro-1,3,4,6,6-pentamethylcyclopenta[c]pyrrole-4-carboxylic acid, m.p. 131°–136° C.

EXAMPLE 32

A stirred solution of 9.0 g. (0.03 mole) of 2-phenyl-2,4,5,6-tetrahydro-1,3,4,6,6-pentamethylcyclopenta[c]pyrrole-4-carboxylic acid (described in Example 31) in 100 ml. of anhydrous tetrahydrofuran was treated with 5.4 g. (0.033 mole) of carbonyldiimidazole and the solution stirred at ambient temperature for eighteen hours. The resulting solution was then treated with 3.5 g. (0.04 mole) of 2-dimethylaminoethylamine in 50 ml. of tetrahydrofuran, and the mixture stirred for an additional six hours. The solution was then concentrated to dryness in vacuo. The residue was partitioned between 200 ml. of water and 100 ml. of ether, and the organic layer was separated, washed with brine, dried, and taken to dryness to give 10.8 g. of 2-phenyl-2,4,5,6-tetrahydro-1,3,4,6,6-pentamethylcyclopenta[c]pyrrole-4-{N-[2-(dimethylamino)-ethyl]}carboxamide as a clear colorless oil.

Following a procedure similar to that described above in Example 32, using the 2-phenyl-2,4,5,6-tetrahydro-1,3,4,6,6-pentamethylcyclopenta[c]pyrrole-4-carboxylic acid described in Example 31 and an appropriate tertiary amino-lower-alkylamine, the following compounds of Formula I, where in each instance $R_2$ is hydrogen; $R_3$, $R_4$, $R_5$ and $R_6$ are $CH_3$; $R_7$ is phenyl; and X is O are prepared.

Table 32

| Example | $R_1$ |
|---|---|
| 32A | $CH_2CH_2N(CH_2CH_3)_2O$ |
| 32B | $CH_2CH_2N(CH_3)_4$ |
| 32C | $CH_2CH_2N(CH_2)_5$ |

EXAMPLE 33

A suspension of 15.0 g. (0.05 mole) of 2-phenyl-2,4,5,6-tetrahydro-1,3,4,6,6-pentamethylcyclopenta[c]pyrrole-4-carboxylic acid (described in Example 31) and 6.0 g. (0.06 mole) of potassium bicarbonate in dimethylformamide was stirred at room temperature for two and one half hours and at 60° C. for a half hour, then cooled and treated with 14 g. (0.1 mole) of methyl iodide in dimethylformamide and the mixture stirred overnight. The resulting dark solution was taken to dryness in vacuo, and the dark residual viscous oil was distilled in vacuo to give 5.9 g. of methyl 2-phenyl-2,4,5,6-tetrahydro-1,3,4,6,6-pentamethylcyclopenta[c]pyrrole-4-carboxylate, b.p. 130°–132° C./0.05 mm.

EXAMPLE 34

A solution of 9.0 g. (0.03 mole) of 2-phenyl-2,4,5,6-tetrahydro-1,3,4,6,6-pentamethylcyclopenta[c]pyrrole-4-carboxylic acid (described in Example 31) in 50 ml. of anhydrous tetrahydrofuran, and the solution treated with 5.4 g. (0.033 mole) of carbonyldiimidazole. The mixture was then treated with a solution of 2.9 g. (0.03 mole) of aniline in 25 ml. of tetrahydrofuran, the solution stirred at room temperature for twenty-four hours, and then taken to dryness in vacuo. The residue was partitioned between water and diethyl ether, and the ether layer was washed with brine, then dried and taken to dryness leaving 10.8 g. of a solid residue which was recrystallized twice from methanol to give 4.7 g. of 1-(2-phenyl-2,4,5,6-tetrahydro-1,3,4,6,6-pentamethylcyclopenta[c]pyrrole-4-yl carbonyl)imidazole, m.p. 134°–136° C.

EXAMPLE 35

A mixture of 29.6 g. (0.1 mole) of 2-phenyl-2,4,5,6-tetrahydro-1,3,4,6,6-pentamethylcyclopenta[c]pyrrole-4-carboxamide (described in Example 20F) and 0.10 g. of cupric acetate monohydrate in 300 ml. of a 4:6 methanol/benzene mixture was stirred under two atmospheres of oxygen for twenty hours. The resulting black solution was taken to dryness, and the residual dark semi-solid was dissolved in 300 ml. of methylene dichloride and the solution washed with water, then with saturated brine, charcoaled, filtered and taken to dryness. The residue was recrystallized twice from methanol to give 14.1 g. of a mixture of 2-phenyl-1-methoxymethyl-2,4,5,6-tetrahydro-3,4,6,6-tetramethylcyclopenta[c]pyrrole-4-carboxamide and 2-phenyl-3-methoxymethyl-2,4,5,6-tetrahydro-1,4,6,6-tetramethylcyclopenta[c]pyrrole-4-carboxamide, m.p. 181°–193° C.

EXAMPLE 36

A mixture of 10 g. (0.032 mole) of 2-phenyl-1-formyl-2,4,5,6-tetrahydro-3,4,6,6-tetramethylcyclopenta[c]pyrrole-4-carboxamide (described in Example 27) and 1.0 g. of 10% palladium-on-charcoal in 100 ml. of 2-(2-ethoxy)-ethoxyethanol was heated to reflux under nitrogen for eight hours and then cooled and allowed to stand at ambient temperature for about twelve hours. The catalyst was removed by filtration, the filtrate poured into water and the mixture extracted with benzene. The benzene extracts, after washing, drying and evaporation to dryness, gave a yellow gum which was triturated with ether and recrystallized from benzene to give 0.9 g. of 2-phenyl-2,4,5,6-tetrahydro-3,4,6,6-tetramethylcyclopenta[c]pyrrole-4-carboxamide, m.p. 186°–190° C.

EXAMPLE 37

2-Phenyl-1-formyl-2,4,5,6-tetrahydro-4,6,6-trimethylcyclopenta[c]pyrrole-4-carboxamide (described in Example 20AY) (2.96 g., 0.01 mole) dissolved in 30 ml. of benzene and 120 ml. of tetrahydrofuran was reacted with 5.7 ml. (0.012 mole) of a 2.1 molar benzene solution of diethyl aluminum cyanide using the procedure described above in Example 17. The product was isolated as an amorphous foam which solidified on trituration with benzene. There was thus obtained 2.75 g. of 2-phenyl-1-(hydroxycyanomethyl)-2,4,5,6-tetrahydro-4,6,6-trimethylcyclopenta[c]pyrrole-4-carboxamide as the hemi-benzene solvate, slowly decomposes at 120° C., resolidifies and melts again at 142° C.

EXAMPLE 38

To a solution of 1.0 g. (0.003 mole) of 2-phenyl-1-hydroxymethyl-2,4,5,6-tetrahydro-4,6,6-trimethylcyclopenta[c]pyrrole-4-carboxamide (described in Example 26A) in 7 ml. of pyridine was added 570 mg. (0.004 mole) of 4-methylbenzoyl chloride. The reaction mixture was refrigerated for two days, poured into saturated sodium bicarbonate solution, extracted with methylene dichloride and the organic extracts dried and evaporated to dryness to give 1.3 g. of residue which was recrystallized from ethyl acetate to give 696 mg. of 2-phenyl-1-(4-methylbenzoyloxymethyl)-2,4,5,6-tetrahydro-4,6,6-trimethylcyclopenta[c]pyrrole-4-carboxamide, m.p. 200–204° C.

Using the procedure described in Example 38, the following compounds of Formula I, where in each case $R_1$, $R_2$ and $R_6$ (3-position) are each hydrogen, $R_3$, $R_4$, and $R_5$ are each $CH_3$ and $R_7$ is $C_6H_5$, were prepared from 2-phenyl-1-hydroxymethyl-2,4,5,6-tetrahydro-4,6,6-trimethylcyclopenta[c]pyrrole-4-carboxamide and acetic anhydride or succinic anhydride.

Table 38

| Example | $R_6(1)$ | Wt. S.M. | Wt. Prod. | m.p.(° C.)/Solvent |
|---|---|---|---|---|
| 38A | $CH_3COOCH_2$ | 2.0 | 1.46 | 174–176/ethyl acetate |
| 38B | $HOOC(CH_2)_2COOCH_2$ | 2.0 | 0.9 | 152–154/ethyl acetate-hexane |

EXAMPLE 39

To a solution of 1 g. (0.0025 mole) of 2-phenyl-1-(3-carboxypropionyloxymethyl)-2,4,5,6-tetrahydro-4,6,6-trimethylcyclopenta[c]pyrrole-4-carboxamide (described in Example 38B) in 10 ml. of tetrahydrofuran at 0–5° C. was added anhydrous ammonia by passing the gas over the surface of the solution. The mixture was diluted with ether and the gummy solid which separated solidified on scratching to give 1.0 g. of the corresponding ammonium salt, m.p. 116°–118° C.

EXAMPLE 40

To a suspension of 2.96 g. (0.01 mole) of 2-phenyl-1-formyl-2,4,5,6-tetrahydro-4,6,6-trimethylcyclopenta[c]pyrrole-4-carboxamide (described in Example 20AY) in 50 ml. of tetrahydrofuran was added 12.9 ml. of a 0.16 molar solution of methyl lithium while cooling the mixture. After stirring for one hour at 0–5° C. and for two hours at ambient temperature, the mixture was poured into ice/aqueous ammonium chloride and extracted with methylene dichloride. The extracts, on drying and evaporation to dryness, gave crude product which was recrystallized from methylene dichloride-heptane to give 1.91 g. of 2-phenyl-1-(1-hydroxyethyl)-2,4,5,6-tetrahydro-4,6,6-trimethylcyclopenta[c]pyrrole-4-carboxamide, m.p. 135°–145° C.

Using a procedure similar to that described in Example 40 above, the following compounds of Formula I where in each case $R_1$ and $R_2$ are each hydrogen, $R_3$, $R_4$ and $R_5$ are each $CH_3$ and $R_7$ is $C_6H_5$ were prepared by reaction of an appropriate organo lithium with either the compound of Example 27 or Example 20AY.

Table 40

| Example | $R_6(1)$ | $R_6(3)$ | Wt.S.M. | Wt.Prod. | m.p.(° C.)/Solvent |
|---|---|---|---|---|---|
| 40A | $CH_3$ | $CHOHCH_3$ | 3.0 | 1.09 | 108–111/ether-hexane |
| 40B | $C_6H_5CHOH$* | H | 2.96 | 2.2 | 198–204/$CH_2Cl_2$-heptane |
| 40C | $CH_2=CHCHOH$ | H | 5.92 | 2.07 | 144–146/benzene |
| 40D | $CH_3$ | $CHOHC_6H_5$ | 6.0 | 4.12 | 151–154/acetonitrile |
| 40E | $CH_3$ | $CHOHCH=CH_2$ | 6.0 | 2.88 | 160–165/ethyl acetate |
| 40F | $C_4H_9CHOH$ | H | 5.92 | 2.4 | 75–80/- |
| 40G | $CH_3$ | $C(CH_3)_2OH$ | 2.0 | 0.68 | 184–186/ether-hexane |
| 40H | $C_2H_5CHOH$ | H | 2.96 | 2.62 | 155–156/ether-heptane |

*Phenyl magnesium bromide used as the organo metallic reagent.

EXAMPLE 41

Reaction of the 2,4,5,6-tetrahydro-1,3,4,6,6-pentamethylcyclopenta[c]pyrrole-4-carbonitriles described in Examples 2, 7, 4A, 4C, 4K, and 8 in an autoclave at 150°–160° C. with an ethanol solution saturated with anhydrous ammonia and anhydrous hydrogen sulfide affords the following compounds of Formula I where, in each instance, $R_1$ and $R_2$ are hydrogen; $R_3$, $R_4$, $R_5$ and $R_6$ are each $CH_3$; and X is S.

Table 41

| Example | $R_7$ |
|---|---|
| 41A | $CH_3$ |
| 41B | $CH_2CH_2CH_2N(CH_3)_2$ |
| 41C | $CH_2CH_2C_6H_5$ |
| 41D | $C_6H_5$ |
| 41E | 2-pyridyl |
| 41F | $CH_2CH_2CSNH_2$ |

EXAMPLE 42

Reaction of the ethyl 4-carbamoyl-2,4,5,6-tetrahydro-1,3,4,6,6-pentamethylcyclopenta[c]pyrrole-2-acetate described above in Example 20AC with alcoholic sodium hydroxide and isolation of the product from an acid or neutral medium affords 4-carbamoyl-2,4,5,6-tetrahydro-1,3,4,6,6-pentamethylcyclopenta[c]pyrrole-2-acetic acid.

EXAMPLE 43

Reaction of the 2-(4-carboxyphenyl)-2,4,5,6-tetrahydro-1,3,4,6,6-pentamethylcyclopenta[c]pyrrole-4-carboxamide described above in Example 20BZ with methanol in the presence of a small amount of a mineral acid affords 2-(4-carbomethoxyphenyl)-2,4,5,6-tetrahydro-1,3,4,6,6-pentamethylcyclopenta[c]pyrrole-4-carboxamide.

EXAMPLE 44

Reaction of the 2-(3-methylmercaptophenyl)-2,4,5,6-tetrahydro-1,3,4,6,6-pentamethylcyclopenta[c]pyrrole-4-carboxamide described above in Example 20CB with one molar equivalent of performic acid in acetone at room temperature affords 2-(3-methylsulfinylphenyl)-2,4,5,6-tetrahydro-1,3,4,6,6-pentamethylcyclopenta[c]pyrrole-4-carboxamide.

EXAMPLE 45

Reaction of 2-(3-methylmercaptophenyl)-2,4,5,6-tetrahydro-1,3,4,6,6-pentamethylcyclopenta[c]pyrrole-4-carboxamide described above in Example 20CB with two molar equivalents of performic acid in acetone at room temperature affords 2-(3-methylsulfonylphenyl)-2,4,5,6-tetrahydro-1,3,4,6,6-pentamethylcyclopenta[c]pyrrole-4-carboxamide.

EXAMPLE 46

Reaction of the 2-phenyl-2,4,5,6-tetrahydro-1,3-diformyl-4,6,6-trimethylcyclopenta[c]pyrrole-4-carboxamide described above in Example 20AB with two molar equivalents of perbenzoic acid in acetone at room temperature affords 2-phenyl-2,4,5,6-tetrahydro-4,6,6-trimethylcyclopenta[c]pyrrole-4-carboxamido-1,3-dicarboxylic acid.

EXAMPLE 47

Reaction of the 2-phenyl-2,4,5,6-tetrahydro-4,6,6-trimethylcyclopenta[c]pyrrole-4-carboxamido-1,3-dicarboxylic acid described above in Example 46 with methanol in the presence of a small amount of a mineral acid affords dimethyl-2-phenyl-2,4,5,6-tetrahydro-4,6,6-trimethylcyclopenta[c]pyrrole-4-carboxamido-1,3-dicarboxylate.

EXAMPLE 48

Reaction of 1-phenyl-2,4,5,6-tetrahydro-1,3,4,6,6-pentamethylcyclopenta[c]pyrrole-4-carbonitrile with one molar equivalent of diisobutyl aluminum hydride in tetrahydrofuran, and, without isolation of the product, oxidation of the resulting material with oxygen affords 2-phenyl-2,4,5,6-tetrahydro-1,3,4,6,6-pentamethylcyclopenta[c]pyrrole-4-carboxamide.

Data obtained on oral administration in rats of the compounds of Formula I in the anti-secretory and the reserpineinduced anti-ulcer tests are given in terms of the % increase in the pH of gastric fluid over control animals and the % reduction in ulcer score over control animals. Doses are expressed in mg./kg., and the compounds are identified by the Example number above where they are disclosed.

| Example | Dose | % pH Increase | % Reduction Ulcer Score |
| --- | --- | --- | --- |
| 20 | 25 | 9 | 60 |
|  | 50 | 50 | 60 |
|  | 100 | 84 | 100 |
|  | 200 | 96 | 100 |
| 20A |  | Inactive | Inactive |
| 20B | 100 | 20 | 40 |
| 20C | 100 | 24 | 0 |
| 20D | 100 | 7 | 0 |
| 20E | 100 | 4 | 0 |
| 20F | 12.5 | 41 | — |
|  | 25 | 52 | 73 |
|  | 50 | 75 | 100 |
|  | 100 | 100 | 100 |
| 20G | 25 | — | 40 |
|  | 50 | 55 | 60 |
|  | 100 | 93 | — |
|  | 100 | 95 | 100 |
| 20H | 25 | 56 | 60 |
|  | 50 | 80 | 100 |
|  | 100 | 93 | 100 |
| 20J | 100 | 4 | 60 |
| 20K | 25 | — | 100 |
|  | 50 | — | 100 |
|  | 100 | 46 | 100 |
|  | 200 | 49 | — |
| 20L | 100 | 10 | 0 |
| 20M | 100 | 16 | 0 |
| 20N | 100 | 35 | 70 |
| 20P | 100 | 45 | 100 |
| 20Q | 100 | 20 | 80 |
| 20R | 100 | 16 | 0 |
| 20S | 100 | 27 | 0 |
| 20T | 50 | — | 80 |
|  | 100 | 47 | 90 |
| 20U | 100 | 9 | 0 |
| 20V | 25 | — | 80 |
|  | 50 | 32 | 100 |
|  | 100 | 45 | — |
|  | 100 | 64 | 100 |
| 20W | 100 | 20 | 20 |
| 20X | 100 | 5 | 0 |
| 20Y | 100 | 145 | 100 |
| 20Z | 100 | 77 | 40 |
| 20AA | 100 | 26 | 40 |
| 20AB | 100 | 18 | 0 |
| 20AC | 100 | 4 | 0 |
| 20AD | 25 | 3 | — |
|  | 50 | 11 | — |
|  | 100 | 16 | 0 |
| 20AE | 50 | 157 | 100 |
|  | 100 | 253 | — |
|  | 200 | 400 | — |
| 20AF | 25 | — | 20 |
|  | 50 | 20 | — |
|  | 100 | 21 | — |
| 20AG | 100 | 0 | 20 |
| 20AH | 100 | 0 | 40 |
| 20AK | 25 | 48 | 20 |
|  | 50 | 110 | — |
|  | 100 | 120 | — |
| 20AL | 25 | 33 | — |
|  | 50 | 75 | 100 |
|  | 100 | 325 | — |
| 20AM | 100 | 0 | 0 |
| 20AN | 100 | 14 | 100 |
| 20AP | 100 | 54 | 80 |
| 20AQ | 50 | 8 | 80 |
| 20AR | 100 | 10 | 20 |
| 20AS | 100 | 18 | 0 |
| 20AT | 100 | 27 | 100 |
| 20AU | 100 | 0 | 0 |
| 20AV | 12.5 | 236 | — |
| 20AW | 50 | — | 40 |
|  | 100 | 68 | — |
| 20AX | 100 | 0 | 0 |
| 20AY | 50 | — | 100 |
|  | 100 | 38 | — |
| 20AZ | 100 | 38 | 40 |
| 20BA | 100 | 0 | 20 |
| 20BB | 100 | 0 | 20 |
| 22 | 100 | 72 | 100 |
| 24 | 100 | 15 | 0 |
| 26 | 100 | 8 | 60 |
| 26A | 12.5 | 45 | — |
|  | 25 | 228 | — |
|  | 50 | 445 | — |

-continued

| Example | Dose | % pH Increase | % Reduction Ulcer Score |
|---|---|---|---|
|  | 100 | 480 | — |
| 26B | 12.5 | 0 | 60 |
|  | 25 | 8 | 80 |
|  | 50 | 163 | — |
|  | 100 | 399 | — |
| 26C | 100 | 14 | 20 |
| 26D | 100 | 0 | 60 |
| 26E | 100 | 42 | 0 |
| 26F | 25 | 0 | — |
|  | 50 | 79 | 80 |
|  | 100 | 244 | — |
| 26G | 100 | 18 | — |
| 26H | 12.5 | 0 | — |
|  | 25 | 45 | — |
|  | 50 | 118 | — |
|  | 100 | 355 | — |
| 27 | 50 | 0 | — |
|  | 100 | — | 0 |
| 28 | 50 | 10 | 100 |
|  | 100 | 140 | — |
| 30 | 100 | 17 | 0 |
| 32 | 50 | — | 0 |
|  | 100 | 16 | 80 |
| 34 | 100 | 0 | 80 |
| 35 | 100 | 51 | 75 |
| 36 | 50 | 0 | — |
|  | 100 | 11 | — |
| 37 | 100 | 188 | — |
| 38 | 100 | 27 | 40 |
| 38A | 100 | 73 | 100 |
| 38B | 100 | 336 | — |
| 39 | 25 | — | 80 |
|  | 50 | 128 | — |
|  | 100 | 166 | — |
|  | 200 | 530 | — |
| 40 | 12.5 | 31 | — |
|  | 25 | 289 | — |
|  | 50 | 565 | — |
|  | 100 | 580 | — |
| 40A | 100 | 16 | — |
| 40B | 100 | 0 | — |
| 40C | 25 | 7 | — |
|  | 50 | 587 | — |
|  | 100 | 600 | — |
| 40D | 100 | 8 | — |
| 40E | 100 | 4 | — |
| 40F | 100 | 24 | — |
| 40G | 100 | 14 | — |
| 40H | 25 | 32 | — |
|  | 50 | 116 | — |
|  | 100 | 458 | — |

We claim:
1. A compound having the formula

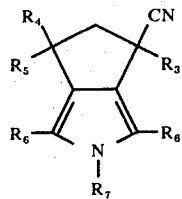

where each of $R_3$, $R_4$ and $R_5$ is hydrogen or methyl; each $R_6$ group is the same or different hydrogen, formyl, and lower-alkane-1,3-diol ketals thereof, phenyl-lower-alkyl, carboxy, carbo-lower-alkoxy, chloromethyl, dichloromethyl, trichloromethyl, hydroxymethyl, hydroxycyanomethyl or lower-alkyl; and $R_7$ is hydrogen, lower-alkyl, halo-lower-alkyl, lower-alkenyl, lower-alkynyl, lower-alkoxy-lower-alkyl, hydroxy-lower-alkyl, lower-alkylthio-lower-alkyl, cycloalkyl, cycloalkyl-lower-alkyl, phenyl, phenyl-lower-alkyl, cyano-lower-alkyl, or divalent-lower-alkylene having its valences on different carbon atoms and joining two of the 2,4,5,6-tetrahydrocyclopenta-[c]pyrrole moieties together, and wherein the phenyl or phenyl-lower-alkyl groups can be further substituted in the phenyl nucleus by a single methylenedioxy or by from one to three members of the group consisting of lower-alkyl, lower-alkoxy, halogen, hydroxy, trifluoromethyl, lower-alkanoylamino, amino, di-lower-alkylamino, carboxyl, carboxamido, carbo-lower-alkoxy, lower-alkyl-mercapto, lower-alkylsulfinyl, lower-alkylsulfonyl, nitro and sulfamoyl.

2. A compound having the formula

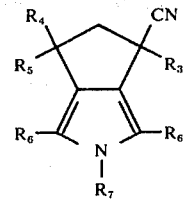

where each of $R_3$, $R_4$ and $R_5$ is hydrogen or methyl; each $R_6$ group is the same or different hydrogen, formyl, and lower-alkane-1,3-diol ketals thereof, hydroxymethyl, carboxy, carbo-lower-alkoxy, chloromethyl, dichloromethyl, trichloromethyl, hydroxycyanomethyl or lower-alkyl; and $R_7$ is hydrogen, lower-alkyl, halo-lower-alkyl, lower-alkenyl, lower-alkynyl, lower-alkoxy-lower-alkyl, hydroxy-lower-alkyl, cycloalkyl, cycloalkyl-lower-alkyl, phenyl, phenyl-lower-alkyl, cyano-lower-alkyl, or divalent-lower-alkylene having its valences on different carbon atoms and joining two of the 2,4,5,6-tetrahydrocyclopenta[c]pyrrole moieties together, and wherein the phenyl or phenyl-lower-alkyl groups can be further substituted in the phenyl nucleus by a single methylenedioxy or by from one to three members of the group consisting of lower-alkyl, lower-alkoxy, halogen, hydroxy, trifluoromethyl, lower-alkanoylamino, amino, di-lower-alkylamino, nitro and sulfamoyl.

3. A compound according to claim 2 having the formula

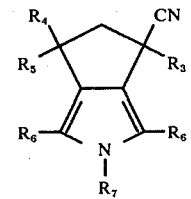

where each of $R_3$, $R_4$ and $R_5$ is hydrogen or methyl; both $R_6$ groups are simultaneously lower-alkyl; and $R_7$ is hydrogen, lower-alkyl, cycloalkyl, cycloalkyl-lower-alkyl, or divalent-lower-alkylene having its valences on different carbon atoms and joining two of the 2,4,5,6-tetrahydrocyclopenta[c]pyrrole moieties together.

4. A compound according to claim 2 having the formula

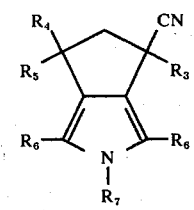

where each of $R_3$, $R_4$ and $R_5$ is hydrogen or methyl; both $R_6$ groups are simultaneously lower-alkyl; and $R_7$ is phenyl, or phenyl-lower-alkyl, and wherein the phenyl or phenyl-lower-alkyl groups can be further substituted in the phenyl nucleus by a single member of the group consisting of lower-alkyl, lower-alkoxy, halogen, hydroxy, methylenedioxy, trifluoromethyl, lower-alkanoylamino, amino, di-lower-alkylamino and sulfamoyl.

5. A compound according to claim 2 having the formula

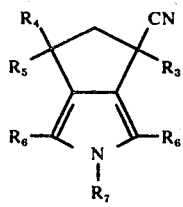

where each of $R_3$, $R_4$ and $R_5$ is hydrogen or methyl; both $R_6$ groups are simultaneously lower-alkyl; and $R_7$ is lower-alkoxy-lower-alkyl, hydroxy-lower-alkyl or cyano-lower-alkyl.

6. A compound according to claim 2 having the formula

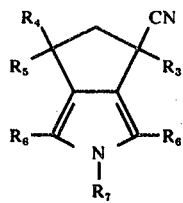

where each of $R_3$, $R_4$ and $R_5$ is hydrogen or methyl; both $R_6$ groups are simultaneously hydrogen, formyl, dichloromethyl, or lower-alkyl; and $R_7$ is phenyl or phenyl-substituted in the phenyl nucleus by a single member of the group consisting of lower-alkyl, lower-alkoxy, halogen, hydroxy, methylenedioxy, trifluoromethyl, lower-alkanoylamino, amino, di-lower-alkylamino and sulfamoyl.

7. 2,4,5,6-Tetrahydro-1,3,4,6,6-pentamethylcyclopenta[c]pyrrole-4-carbonitrile according to claim 3.

8. 2,4,5,6-Tetrahydro-1,2,3,4,6,6-hexamethylcyclopenta[c]pyrrole-4-carbonitrile according to claim 3.

9. 2-Ethyl-2,4,5,6-tetrahydro-1,3,4,6,6-pentamethylcyclopenta[c]pyrrole-4-carbonitrile according to claim 3.

10. 2-Propyl-2,4,5,6-tetrahydro-1,3,4,6,6-pentamethylcyclopenta[c]pyrrole-4-carbonitrile according to claim 3.

11. 2-Butyl-2,4,5,6-tetrahydro-1,3,4,6,6-pentamethylcyclopenta[c]pyrrole-4-carbonitrile according to claim 3.

12. 2-Isopropyl-2,4,5,6-tetrahydro-1,3,4,6,6-pentamethylcyclopenta[c]pyrrole-4-carbonitrile according to claim 3.

13. 2-Cyclohexyl-2,4,5,6-tetrahydro-1,3,4,6,6-pentamethylcyclopenta[c]pyrrole-4-carbonitrile according to claim 3.

14. 2-Cyclopropyl-2,4,5,6-tetrahydro-1,3,4,6,6-pentamethylcyclopenta[c]pyrrole-4-carbonitrile according to claim 3.

15. 2-Cyclopentyl-2,4,5,6-tetrahydro-1,3,4,6,6-pentamethylcyclopenta[c]pyrrole-4-carbonitrile according to claim 3.

16. 2-Cyclobutyl-2,4,5,6-tetrahydro-1,3,4,6,6-pentamethylcyclopenta[c]pyrrole-4-carbonitrile according to claim 3.

17. 2,2'-Hexamethylenebis[2,4,5,6-tetrahydro-1,3,4,6,6-pentamethylcyclopenta[c]pyrrole-4-carbonitrile]according to claim 3.

18. 2-Phenyl-2,4,5,6-tetrahydro-1,3,4,6,6-pentamethylcyclopenta[c]pyrrole-4-carbonitrile according to claim 4.

19. 2-(4-Methoxyphenyl)-2,4,5,6-tetrahydro-1,3,4,6,6-pentamethylcyclopenta[c]pyrrole-4-carbonitrile according to claim 4.

20. 2-(4-Methylphenyl)-2,4,5,6-tetrahydro-1,3,4,6,6-pentamethylcyclopenta[c]pyrrole-4-carbonitrile according to claim 4.

21. 2-(4-Chlorophenyl)-2,4,5,6-tetrahydro-1,3,4,6,6-pentamethylcyclopenta[c]pyrrole-4-carbonitrile according to claim 4.

22. 2-(3-Chlorophenyl)-2,4,5,6-tetrahydro-1,3,4,6,6-pentamethylcyclopenta[c]pyrrole-4-carbonitrile according to claim 4.

23. 2-(3-Methylphenyl)-2,4,5,6-tetrahydro-1,3,4,6,6-pentamethylcyclopenta[c]pyrrole-4-carbonitrile according to claim 4.

24. 2-(2-Chlorophenyl)-2,4,5,6-tetrahydro-1,3,4,6,6-pentamethylcyclopenta[c]pyrrole-4-carbonitrile according to claim 4.

25. 2-(2-Methylphenyl)-2,4,5,6-tetrahydro-1,3,4,6,6-pentamethylcyclopenta[c]pyrrole-4-carbonitrile according to claim 4.

26. 2-(4-Fluorophenyl)-2,4,5,6-tetrahydro-1,3,4,6,6-pentamethylcyclopenta[c]pyrrole-4-carbonitrile according to claim 4.

27. 2-(4-Dimethylaminophenyl)-2,4,5,6-tetrahydro-1,3,4,6,6-pentamethylcyclopenta[c]pyrrole-4-carbonitrile according to claim 4.

28. 2-(4-Hydroxyphenyl)-2,4,5,6-tetrahydro-1,3,4,6,6-pentamethylcyclopenta[c]pyrrole-4-carbonitrile according to claim 4.

29. 2-(4-Acetylaminophenyl)-2,4,5,6-tetrahydro-1,3,4,6,6-pentamethylcyclopenta[c]pyrrole-4-carbonitrile according to claim 4.

30. 2-(4-Sulfamylphenyl)-2,4,5,6-tetrahydro-1,3,4,6,6-pentamethylcyclopenta[c]pyrrole-4-carbonitrile according to claim 4.

31. 2-(2-Phenethyl)-2,4,5,6-tetrahydro-1,3,4,6,6-pentamethylcyclopenta[c]pyrrole-4-carbonitrile according to claim 4.

32. 2-Benzyl-2,4,5,6-tetrahydro-1,3,4,6,6-pentamethylcyclopenta[c]pyrrole-4-carbonitrile according to claim 4.

33. 2-(2-Cyanoethyl)-2,4,5,6-tetrahydro-1,3,4,6,6-pentamethylcyclopenta[c]pyrrole-4-carbonitrile according to claim 5.

34. 2-(2-Ethoxyethyl)-2,4,5,6-tetrahydro-1,3,4,6,6-pentamethylcyclopenta[c]pyrrole-4-carbonitrile according to claim 5.

35. 2-(3-Hydroxypropyl)-2,4,5,6-tetrahydro-1,3,4,6,6-pentamethylcyclopenta[c]pyrrole-4-carbonitrile according to claim 5.

36. 2-Phenyl-2,4,5,6-tetrahydro-1,3-diformyl-4,6,6-trimethylcyclopenta[c]pyrrole-4-carbonitrile according to claim 6.

37. 2-Phenyl-2,4,5,6-tetrahydro-1,3-bis-dichloromethyl-4,6,6-trimethylcyclopenta[c]pyrrole-4-carbonitrile according to claim 6.

38. 2-Phenyl-2,4,5,6-tetrahydro-4,6,6-trimethylcyclopenta[c]pyrrole-4-carbonitrile according to claim 6.

* * * * *

UNITED STATES PATENT AND TRADEMARK OFFICE
CERTIFICATE OF CORRECTION

PATENT NO. : 4,008,250

DATED : February 15, 1977

INVENTOR(S) : Malcolm R. Bell and Rudolf Oesterlin

It is certified that error appears in the above—identified patent and that said Letters Patent are hereby corrected as shown below:

Column 2, lines 46 and 47 reads "1,3-di-$R_6$-2-$R_7$-4-$R_3$-6-$R_4$-6$R_5$-2,4,5,6-" should read --1,3-di-$R_6$-2-$R_7$-4-$R_3$-6-$R_4$-6-$R_5$-2,4,5,6,- --.

Column 3, line 31 reads "is the same of different" should read --is the same or different--.

Column 6, line 31 reads "quaternary slt" should read --quaternary salt--.

Column 12, lines 13-14 reads "while other transformation are carried" should read --while other transformations are carried--.

U NITED STATES PATENT AND TRADEMARK OFFICE
CERTIFICATE OF CORRECTION

PATENT NO. : 4,008,250  Page 2 of 2
DATED : February 15, 1977
INVENTOR(S) : Malcolm R. Bell and Rudolf Oesterlin It is certified that error appears in the above—identified patent and that said Letters Patent are hereby corrected as shown below:

Page two

Column 14, line 36 last structure:

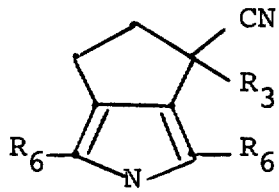  should read  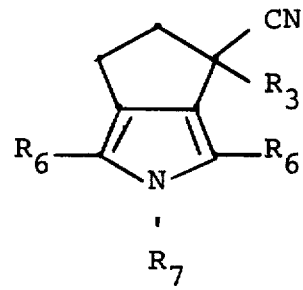

Column 20, line 44 reads "$\leq$ 3mm. 5 points" should read -- $\geq$ 3mm.$^2$ 5 points --.

Signed and Sealed this

Third Day of July 1979

[SEAL]

Attest:

LUTRELLE F. PARKER

Attesting Officer    Acting Commissioner of Patents and Trademarks